United States Patent
Patzoldt et al.

(10) Patent No.: US 8,648,012 B2
(45) Date of Patent: Feb. 11, 2014

(54) HERBICIDAL COMPOSITIONS COMPRISING NAPTALAM

(75) Inventors: William L. Patzoldt, Raleigh, NC (US); Steven Bowe, Apex, NC (US); Leon Duchene, Raleigh, NC (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/147,024

(22) PCT Filed: Feb. 1, 2010

(86) PCT No.: PCT/EP2010/051161
§ 371 (c)(1), (2), (4) Date: Jul. 29, 2011

(87) PCT Pub. No.: WO2010/086437
PCT Pub. Date: Aug. 5, 2010

(65) Prior Publication Data
US 2011/0287935 A1    Nov. 24, 2011

Related U.S. Application Data

(60) Provisional application No. 61/149,058, filed on Feb. 2, 2009.

(51) Int. Cl.
*A01N 43/40* (2006.01)
*A01N 43/60* (2006.01)

(52) U.S. Cl.
USPC .......................................... 504/130; 504/136

(58) Field of Classification Search
None
See application file for complete search history.

(56) References Cited

U.S. PATENT DOCUMENTS 6,534,444 B1 *  3/2003  Sievernich et al. ........... 504/128
7,563,749 B2 *  7/2009  Hills et al. .................... 504/223

FOREIGN PATENT DOCUMENTS

| EP | 0 646 315 | 4/1995 |
| GB | 1 063 234 | 3/1967 |
| JP | 2008285451 | * 11/2008 |

OTHER PUBLICATIONS

International Search Report prepared in International Application No. PCT/EP2010/051161, filed Feb. 1, 2010.
International Preliminary Report on Patentability from corresponding International Application No. PCT/EP2010/051161, filed Feb. 1, 2010.
Grossmann et al., "On the mechanism of selectivity of the corn herbicide BAS 662H: a combination of the novel auxin transport inhibitor diflufenzopyr and the auxin herbicide dicamba", Pest Management Science, (2002), pp. 1002-1014, vol. 58, Search Report.
Lym et al., "Diflufenzopyr increases perennial weed control with auxin herbicides", Proceedings of the Western Society of Weed Science, (1998), pp. 59-62, vol. 51, Search Report.
Miller et al., Cross-resistance in and chemical control of auxinic herbicide-resistant yellow starthistle (*Centaurea solstitialis*)[1], Weed Technology, (2001), pp. 293-299, vol. 15, Search Report.
Oliver et al., "Overtop herbicide applications for cocklebur control in soybean", Proceedings, Southern Weed Science Society, (1976), pp. 96-102, vol. 29, Search Report.
Prendeville et al., "Antagonistic responses with combinations of carbamate and growth regulator herbicides[1]", Weed Science, Weed Science Society of America, (1969), pp. 307-309, vol. 17, Search Report.
Tomlin (Ed.), "Naptalam", The Pesticide Manual, 14th ed., (2006), pp. 746-747.

* cited by examiner

*Primary Examiner* — Alton Pryor
(74) *Attorney, Agent, or Firm* — Brinks Gilson & Lione

(57) ABSTRACT

The present invention relates to herbicidal compositions comprising a) a herbicide compound A which is selected from N/-1-naphthylphthalamic acid (naptalam), the salts and esters thereof; and b) a herbicide compound B which is selected from b.1 3,6-dichloro-2-methoxybenzoic acid (dicamba), the salts and esters thereof; b.2 quinolinecarboxylic acid herbicides; b.3 pyridinecarboxylic acid herbicides; and b.4 aminocyclopyrachlor, the salts and esters thereof. The present invention also relates to the use of these compositions for controlling undesirable vegetation, in particular in crops, in turf or pasture, in rangeland, in fallow, or in forestry.

20 Claims, No Drawings

HERBICIDAL COMPOSITIONS COMPRISING NAPTALAM

This application is a National Stage application of International Application No. PCT/EP2010/051161, filed Feb. 1, 2010, the entire contents of which is hereby incorporated herein by reference. This application also claims priority under 35 U.S.C. §119(e) to U.S. Provisional Application No. 61/149,058, filed Feb. 2, 2009, the entire contents of which is hereby incorporated herein by reference.

The present invention relates to herbicidal compositions comprising naptalam and at least one further herbicidal compound. The present invention also relates to the use of these compositions for controlling undesirable vegetation, in particular in crops and non-crop areas.

BACKGROUND OF THE INVENTION

In crop protection, it is principally desirable in principle to increase the specificity and the reliability of the action of active compounds. In particular, it is desirable for the crop protection product to control the harmful plants effectively and, at the same time, to be tolerated by the useful plants in question.

Naptalam, i.e. N-1-naphthylphthalamic acid [IUPAC], sometimes also termed as NPA or Alanap™, its salts and esters such as naptalam-sodium are well known herbicide active compounds (see C. D. S Tomlin (Ed.), The Pesticide Manual, 14th ed., 2006, BCPC Alton, Hampshire, UK, pp. 746 f.). Naptalam is known to possess herbicidal action against broadleaf weeds and some grasses.

Historically, naptalam was used as a preemergence and postemergence herbicide alone or in combination with other herbicides at application rates of 2000 to 5500 g/ha (see "The Pesticide Manual" loc. cit). However, the herbicidal activity and the activity spectrum are limited and the required application rates are high by contemporary standards.

GB 1,063,234 suggests a combined application of naptalam or its salts with phenoxyaliphatic carboxylic acid herbicides such as 2,4-dichlorophenoxyacetic acid (2,4-D), (2,4,5-trichlorophenoxy)acetic acid (2,4,5-T), 2-methyl-4-chlorophenoxyacetic acid (MCPA), 2-(2-methyl-4-chlorophenoxy)propionic acid (mecoprop), 4-(2,4-dichlorophenoxy)butyric acid (2,4-DB) or salts thereof. The activity spectra of the mixtures are shown to be broader than the activity spectrum of the individual compounds.

A formulation containing naptalam and 2,4-DB was commercially available under the tradename Rescue® from Chemtura. The formulation had been suggested for controlling broadleaf weeds in crops of soybean.

Furthermore, it has been suggested to co-apply naptalam with one of the following herbicides: clomazone, halosulfuron-methyl, bensulide, chlorothal, trifluralin, ethalfluralin or clomazone plus ethalfluralin.

From EP 646315 it is known that the herbicidal activity of certain herbicides can be increased by the combined application with certain herbicidal semicarbazones, such as diflufenzopyr, which belongs to the group of auxin transport inhibitors (group P of the HRAC classification system: HRAC, Classification of Herbicides According to Mode of Action, http://www.plantprotection.org/hrac/MOA.html). Unfortunately, the combined application of these herbicidal semicarbazones with certain other herbicides in certain crops such as cereals, cotton, soybean or turf leads to damage of the crop plants.

SUMMARY OF THE INVENTION

It is an object of the present invention to provide herbicidal compositions, which show enhanced herbicide action against undesirable harmful plants and/or to improve the compatibility with crop plants, in particular improved compatibility with cereals, soybean, oilseed crops, pulse crops, forage crops, cotton, turf and/or pasture. The composition should have a good post-emergence herbicidal activity. The compositions should also show an accelerated action on harmful plants, i.e. they should damage harmful plants more quickly when compared with application of the individual herbicides.

We have found that these and further objects are achieved, surprisingly, by herbicidally active compositions comprising
a) a herbicide compound A which is selected from N-1-naphthylphthalamic acid (naptalam), the salts and esters thereof; and
b) a herbicide compound B which is selected from
  b.1 3,6-dichloro-2-methoxybenzoic acid (dicamba), the salts and esters thereof;
  b.2 quinolinecarboxylic acid herbicides;
  b.3 pyridinecarboxylic acid herbicides; and
  b.4 aminocyclopyrachlor, the salts and esters thereof.

The invention particularly relates to compositions in the form of herbicidally active compositions as defined above.

The invention furthermore relates to the use of a composition as defined herein for controlling undesirable vegetation in crops and non-crop areas. When using the compositions of the invention for this purpose the herbicide compound A and the herbicide compound B and, if present, the herbicide component C (as defined hereinafter) and/or the safener D (as defined hereinafter) can be applied simultaneously or in succession to the areas, where undesirable vegetation occurs or may occur. The compounds A and B and optionally C and/or D are in particular applied in crops, where undesirable vegetation may occur.

The invention furthermore relates to the use of a composition as defined herein for controlling undesirable vegetation in crops which, by genetic engineering or by breeding, are resistant to one or more herbicides and/or pathogens such as harmful fungi, and/or to attack by insects; preferably resistant to one or more synthetic auxin herbicides and/or resistant to one or more of the herbicides mentioned below.

The invention furthermore relates to a method for controlling undesirable vegetation, which comprises applying a herbicidal composition according to the present invention to the undesirable plants. Application can be done before, during and/or after, preferably during and/or after, the emergence of the undesirable plants. The herbicide compound A and the herbicide compound B, and, if present, the herbicide component C and/or the safener D can be applied simultaneously or in succession.

The invention in particular relates to a method for controlling undesirable vegetation in crops, which comprises applying an herbicidal composition according to the present invention in crops where undesirable vegetation occurs or might occur.

The invention also relates to a method for controlling undesirable vegetation in non-crop areas, including application in turf, pasture, fallow or rangeland, and rights-of way applications, which method comprises applying a herbicidal composition according to the present invention to the non-crop areas where undesirable vegetation occurs or might occur. Application in rights-of-way includes any application of the herbicide composition for controlling undesirable vegetation occurring in traffic infrastructure e.g. application to railroads, country roads, dirt tracks, field path, wayside and the like, where undesirable vegetation occurs or is likely to occur.

The invention also relates to a method for controlling undesirable vegetation in forestry, which comprises applying an herbicidal composition according to the present invention in forests where undesirable vegetation occurs or might occur or in sites where trees shall be planted (site preparation).

The invention furthermore relates to a method for controlling undesirable vegetation, which comprises allowing a composition according to the present invention to act on plants, their habitat or on seed.

In the methods of the present invention it is immaterial whether the herbicide compound A, and the herbicide compound B and, if present, a herbicide component C and/or the safener D are formulated and applied jointly or separately. In the case of separate application it is of minor importance, in which order the application takes place. It is only necessary, that the herbicide compound A and the herbicide compound B and, if present, the herbicide component C and/or the safener D are applied in a time frame that allows simultaneous action of the active ingredients on the plants, preferably within a time-frame of at most 14 days, in particular at most 7 days.

The invention also relates to an herbicide formulation, which comprises a herbicidally active composition as defined herein and at least one carrier material, including liquid and/or solid carrier materials.

DETAILED DESCRIPTION OF THE INVENTION

Surprisingly, the compositions according to the present invention have better herbicidal activity against harmful plants than would have been expected by the herbicidal activity of the individual compounds. In other words, the joint action of naptalam, a salt or ester thereof and the herbicide compound B results in an enhanced activity against harmful plants in the sense of a synergy effect (synergism or potentiation), even at low application rates of naptalam. For this reason, the compositions can, based on the individual components, be used at lower application rates to achieve a herbicidal effect comparable to the individual components. Furthermore, the compositions of the present invention provide an accelerated action on harmful plants, i.e. they effect damaging of the harmful plants more quickly in comparison with application of the individual herbicides. Presumably, the accelerated or increased activity of herbicides results from the concentration of both herbicide compound A and herbicide compound B and, if present, the herbicide compound C in plant meristematic tissues, thus leading to plant death.

Moreover, the compositions of the present invention provide good pre- and post-emergence herbicidal activity, i.e. the compositions are particularly useful for combating/controlling harmful plants after their emergence. The compositions of the present invention also show good crop compatibility, i.e. their use in crops does not result in increased damage when compared to the individual application of the herbicide compounds A or B.

As used herein, the terms "controlling" and "combating" are synonyms.

As used herein, the terms "undesirable vegetation" and "harmful plants" are synonyms.

If the compounds mentioned as herbicide compounds A, B, C and safeners D (for C and D see below) have functional groups, which can be ionized, they can also be used in the form of their agriculturally acceptable salts.

In general, the salts of those cations are suitable whose cations have no adverse effect on the action of the active compounds ("agriculturally acceptable").

Preferred cations are the ions of the alkali metals, preferably of lithium, sodium and potassium, of the alkaline earth metals, preferably of calcium and magnesium, and of the transition metals, preferably of manganese, copper, zinc and iron, furthermore ammonium and substituted ammonium (hereinafter also termed as organoammonium) in which one to four hydrogen atoms are replaced by $C_1$-$C_8$-alkyl, $C_1$-$C_4$-alkyl, hydroxy-$C_1$-$C_4$-alkyl, in particular hydroxy-$C_2$-$C_4$-alkyl, $C_1$-$C_4$-alkoxy-$C_1$-$C_4$-alkyl, in particular $C_1$-$C_4$-alkoxy-$C_2$-$C_4$-alkyl, hydroxy-$C_1$-$C_4$-alkoxy-$C_1$-$C_4$-alkyl, in particular hydroxy-$C_2$-$C_4$-alkoxy-$C_2$-$C_4$-alkyl, phenyl or benzyl, preferably ammonium, methylammonium, isopropylammonium, dimethylammonium, diisopropylammonium, trimethylammonium, tetramethylammonium, tetraethylammonium, tetrabutylammonium, pentylammonium, hexylammonium, heptylammonium, 2-hydroxyethylammonium (olamine salt), 2-(2-hydroxyethoxy)eth-1-ylammonium (diglycolamine salt), di(2-hydroxyeth-1-yl)ammonium (=diethanolammonium salt or diolamine salt), tri(2-hydroxyethyl)ammonium (=triethanolammonium salt or trolamine salt), mono-, di- and tri(hydroxypropyl)ammonium (=mono-, di- and tripropanolammonium), benzyltrimethylammonium, benzyltriethylammonium, furthermore phosphonium ions, sulfonium ions, preferably tri($C_1$-$C_4$-alkyl)sulfonium such as trimethylsulfonium, and sulfoxonium ions, preferably tri($C_1$-$C_4$-alkyl)sulfoxonium.

In the compositions according to the invention, the compounds that carry a carboxyl group can also be employed in the form of agriculturally acceptable derivatives, for example as amides such as mono- or di-$C_1$-$C_6$-alkylamides or arylamides, as esters, for example as allyl esters, propargyl esters, $C_1$-$C_{10}$-alkyl esters or alkoxyalkyl esters, and also as thioesters, for example as $C_1$-$C_{10}$-alkyl thioesters. Preferred mono- and di-01-06-alkylamides are the methyl- and the dimethylamides. Preferred arylamides are, for example, the anilidines and the 2-chloroanilides. Preferred alkyl esters are, for example, the methyl, ethyl, propyl, isopropyl, butyl, isobutyl, pentyl, mexyl (1-methylhexyl) or isooctyl (2-ethylhexyl) esters. Preferred $C_1$-$C_4$-alkoxy-$C_1$-$C_4$-alkyl esters are the straight-chain or branched $C_1$-$C_4$-alkoxyethyl esters, for example the methoxyethyl, ethoxyethyl or butoxyethyl (butoyl) esters. An example of the straight-chain or branched $C_1$-$C_{10}$-alkyl thioesters is the ethyl thioester. Preferred derivatives are the esters.

The compositions of the invention comprise naptalam, a salt or ester thereof as a first component a). Suitable salts of naptalam include those salts of naptalam, where the counterion is an agriculturally acceptable cation. Suitable salts of naptalam are the alkalimetal salts of naptalam, in particular the sodium salt (naptalam-sodium) and the potassium salt, and the ammonium or substituted ammonium salts, in particular the ammonium salt, the diethanolammonium salt (naptalam-diolamine), the diglycolammonion salt (naptalam-diglycolamine), the isopropylammonium salt, the dimethylammonium salt or the triethanolammonium salt (naptalam-trolamin).

As a second component b), the compositions of the invention comprise a herbicide compound B which is selected from:

b.1 3,6-dichloro-2-methoxybenzoic acid (dicamba), the salts and esters thereof;
b.2 quinolinecarboxylic acid herbicides;
b.3 pyridinecarboxylic acid herbicides; and
b.4 aminocyclopyrachlor (IUPAC: 6-amino-5-chloro-2-cyclopropylpyrimidine-4-carboxylic acid, CAS 858956-08-8), the salts and esters thereof.

The herbicide compounds mentioned in the groups b.1, b.2, b.3 and b.4 belong to the group of synthetic auxins or auxin agonists, respectively. Synthetic auxins are compounds which act like phytohormones, such indole-3-acetic acid. Synthetic auxins belong to the group O of the HRAC classification system (see HRAC, Classification of Herbicides According to Mode of Action, http://www.plantprotection.org/hrac/MOA.html).

Suitable salts of dicamba include those salts of dicamba, where the counterion is an agriculturally acceptable cation. Suitable examples of such salts are dicamba-sodium, dicamba-potassium, dicamba-methylammonium, dicamba-isopropylammonium, dicamba-diglycolamine, dicamba-olamine, dicamba-diolamine and dicamba-trolamine. Examples of a suitable ester are dicamba-methyl and dicamba-butoyl.

Quinolinecarboxylic acid herbicides herbicides (b.2) include e.g. quinclorac and quinmerac and the salts and esters thereof. Examples of suitable salts of quinclorac and quinmerac include e.g. their sodium salts, potassium salts, ammonium salts or substituted ammonium salts as defined above, in particular mono-, di- and tri-$C_1$-$C_8$-alkylammonium salts such as methylammonium, dimethylammonium and isopropylammonium, mono-, di- and tri-hydroxy-$C_2$-$C_8$-alkylammonium salts such as hydroxyethylammonium, di(hydroxyethyl)ammonium, tri(hydroxyethyl)ammonium, hydroxypropylammonium, di(hydroxypropyl)ammonium and tri(hydroxypropyl)ammonium salts, their diglycolamine salts and their esters, in particular its $C_1$-$C_8$-alkyl esters and $C_1$-$C_4$-alkoxy-$C_2$-$C_4$-alkyl esters, such as methylesters, ethylesters, iso-propyl, butyl, hexyl, heptyl, iso-heptyl, isooctyl, 2-ethylhexyl and butoxyethyl esters.

Pyridinecarboxylic acid herbicides (b.3) include e.g. aminopyralid, clopyralid, picloram, triclopyr and fluoroxypyr and their salts and their esters. Examples of suitable salts of aminopyralid, clopyralid, picloram, triclopyr and fluoroxypyr include e.g. their sodium salts, potassium salts, ammonium salts or substituted ammonium salts as defined above, in particular mono-, di- and tri-$C_1$-$C_8$-alkylammonium salts such as methylammonium, dimethylammonium and isopropylammonium, mono-, di- and tri-hydroxy-$C_2$-$C_8$-alkylammonium salts such as hydroxyethylammonium, di(hydroxyethyl)ammonium, tri(hydroxyethyl)ammonium, hydroxypropylammonium, di(hydroxypropyl)ammonium and tri(hydroxypropyl)ammonium salts, their diglycolamine salts and their esters, in particular its $C_1$-$C_8$-alkyl esters and $C_1$-$C_4$-alkoxy-$C_2$-$C_4$-alkyl esters, such as methylesters, ethylesters, iso-propyl, butyl, hexyl, heptyl, iso-heptyl, isooctyl, 2-ethylhexyl and butoxyethyl esters. Suitable examples of such salts and esters are aminopyralid-potassium, aminopyralid-tris(2-hydroxypropyl)ammonium, clopyralid-potassium, clopyralid-olamine, clopyralid-tris(2-hydroxypropyl) ammonium, clopyralid-methyl, picloram-potassium, picloram-triethylammonium, picloram-tris(2-hydroxypropyl)ammonium, picloram-methyl, picloram-2-ethylhexyl, picloram-isooctyl, fluoroxypyr-meptyl, fluroxypyrbutomethyl, triclopyr-triethylammonium, triclopyr-ethyl and triclopyr-butotyl.

Suitable salts of aminocyclopyrachlor include those salts, where the counterion is an agriculturally acceptable cation as mentioned above. Suitable examples of such salts are aminocyclopyrachlor-sodium, aminocyclopyrachlor-potassium. Examples of suitable esters include aminocyclopyrachlor-methyl.

The compositions of the present invention may also contain one or more, e.g. 1, 2, 3 or 4, in particular 1 or 2 further herbicide compounds C. These one or more further herbicide compounds C are hereinafter also termed as herbicide component C. A further herbicide compound C or component C means that the herbicide compounds of component C is/are different from the herbicides already present in the composition, i.e. the herbicide compound C or the herbicide component C is different from naptalam, its salts and esters and it is also different from the herbicide compound B, its salts and esters, which is already present in the composition.

Preferably, the one or more further herbicide compounds C is/are selected from herbicide compounds which belong to the group of synthetic auxins/auxin agonists. Examples of synthetic auxins/auxin agonists, which are suitable as herbicide component of component C include e.g.:

c.1 benzoic acid herbicides, in particular dicamba, tricamba, chloramben or 2,3,6-TBA (2,3,6-trichlorobenzoic acid) and the salts and esters thereof;

c.2 quinolinecarboxylic acid herbicides as mentioned before, in particular quinclorac or quinmerac and the salts and esters thereof as mentioned above;

c.3 pyridinecarboxylic acid herbicides, in particular aminopyralid, clopyralid, picloram, triclopyr or fluoroxypyr and the salts and esters thereof as mentioned above;

c.4 aminocyclopyrachlor, the salts and esters thereof as mentioned above; and c.5 phenoxycarboxylic acid herbicides, e.g. phenoxyacetic acid herbicides such as 2,4-D, 3,4-DA, MCPA, 2,4,5-T, phenoxypropionic acid herbicides such as 2,4-DP (dichlorprop), 2,4-DP-P, 4-CPP, 3,4-DP, fenoprop, CMPP (mecoprop), CMPP-P, and phenoxybutyric acid herbicides such as 4-CPB, 2,4-DB, 3,4-DB, 2,4,5-TB, MCPB, their salts and their esters, in particular one of the following phenoxycarboxylic acid herbicides: 2,4-D, 2,4-DB, 2,4-DP (dichlorprop), 2,4-DP-P, MCPP (mecoprop), MCPP-P, MCPA, MCPB, their salts and their esters;

and mixtures thereof.

Suitable salts of benzoic acid herbicides include the salts of dicamba, tricamba, chloramben and 2,3,6-TBA (2,3,6-trichlorobenzoic acid) with agriculturally acceptable cations, in particular their sodium salts, potassium salts, ammonium salt or substituted ammonium salts as defined above, in particular mono-, di- and tri-$C_1$-$C_8$-alkylammonium salts such as methylammonium, dimethylammonium and isopropylammonium, 2-(2-hydroxyethoxy)eth-1-ylammonium, mono-, di- and tri-(hydroxy-$C_2$-$C_4$-alkyl)ammonium salts such as 2-hydroxyethylammonium, di(2-hydroxy-ethyl)ammonium, tri(2-hydroxyethyl)ammonium, hydroxypropylammonium, di(hydroxypropyl)ammonium and tri(hydroxypropyl)ammonium salts. Suitable esters are e.g. the $C_1$-$C_8$-alkyl esters and $C_1$-$C_4$-alkoxy-$C_2$-$C_4$-alkyl esters, such as methylesters, ethylesters, iso-propyl, butyl, hexyl, heptyl, iso-heptyl, isooctyl, 2-ethylhexyl and butoxyethyl esters. Suitable examples of such salts are dicamba-sodium, dicamba-potassium, dicamba-methylammonium, dicamba-isopropylammonium, dicamba-olamine, dicamba-diolamine, dicamba-diglycolamine, dicamba-trolamine, tricamba-sodium, tricamba-potassium, tricamba-methylammonium, tricamba-isopropylammonium, tricamba-olamine, tricamba-diolamine, tricamba-trolamine, chloramben-ammonium, chloramben-methylammonium, chloramben-sodium, chloramben-diolamine, 2,3,6-T-sodium, 2,3,6-dimethylammonium. Suitable examples of such esters are dicamba-methyl, dicamba-butoyl and chloramben-methyl.

Suitable salts of phenoxycarboxylic acid herbicides include the salts of these compounds with an agriculturally acceptable cations, in particular their alkali metal salts, such as lithium salts, sodium salts or potassium salts, ammonium salt or substituted ammonium salts as defined above, in particular mono-, di- and tri-$C_1$-$C_8$-alkylammonium salts such as methylammonium, dimethylammonium and isopropylammonium, 2-(2-hydroxyethoxy)eth-1-ylammonium, mono-, di- and tri-(hydroxy-$C_2$-$C_4$-alkyl)ammonium salts such as hydroxyethylammonium, di(hydroxylethyl)ammonium, tri(hydroxyethyl)ammonium, hydroxypropylammonium, di(hydroxypropyl)ammonium and tri(hydroxypropyl)ammonium salts. Suitable esters are e.g. the $C_1$-$C_8$-alkyl esters and $C_1$-$C_4$-alkoxy-$C_2$-$C_4$-alkyl esters, such as methylesters, ethylesters, iso-propyl, butyl, hexyl, heptyl, iso-heptyl, isooctyl, 2-ethylhexyl and butoxyethyl esters. Examples of salts and esters include e.g. 2,4-D-ammonium, 2,4-D-butotyl, 2,4-D-2-butoxypropyl, 2,4-D-3-butoxypropyl, 2,4-D-butyl, 2,4-D-diethylammonium, 2,4-D-dimethylammonium, 2,4-D-diolamine, 2,4-D-dodecylammonium, 2,4-D-ethyl, 2,4-D-2-ethylhexyl, 2,4-D-heptylammonium, 2,4-D-isobutyl, 2,4-D-isoctyl, 2,4-D-isopropyl, 2,4-D-isopropylammonium, 2,4-D-lithium, 2,4-D-meptyl, 2,4-D-methyl, 2,4-D-octyl, 2,4-D-pentyl, 2,4-D-propyl, 2,4-D-sodium, 2,4-D-tefuryl, 2,4-D-tetradecylammonium, 2,4-D-triethylammonium, 2,4-D-tris(2-hydroxypropyl)ammonium, 2,4-D-trolamine, MCPA-butotyl, MCPA-butyl, MCPA-dimethylammonium, MCPA-diolamine, MCPA-ethyl, MCPA-2-ethylhexyl, MCPA-isobutyl, MCPA-isoctyl, MCPA-isopropyl, MCPA-methyl, MCPA-olamine, MCPA-potassium, MCPA-sodium, MCPA-trolamine, dichlorprop-butotyl, dichlorprop-dimethylammonium, dichlorprop-ethylammonium, dichlorprop-2-ethylhexyl, dichlorprop-isoctyl, dichlorprop-methyl, dichlorprop-potassium, dichlorprop-sodium, dicloprop-P-dimethylammonium, mecoprop-dimethylammonium, mecoprop-diolamine, mecoprop-ethadyl, mecoprop-isoctyl, mecoprop-methyl, mecoprop-potassium, mecoprop-sodium, mecoprop-trolamine, mecoprop-P-dimethylammonium, mecoprop-P-isobutyl, mecoprop-P-potassium, MCPB-methyl, MCPB-ethyl and MCPB-sodium.

Preferred phenoxycarboxylic acid herbicides include 2,4-D, 2,4-DB, 2,4-DP (dichlorprop), 2,4-DP-P, MCPP (mecoprop), MCPP-P, MCPA, MCPB, their salts and their esters.

The compositions of the invention may also comprise, as a component D, one or more safeners. Safeners, also termed as herbicide safeners, are organic compounds which in some cases lead to better crop plant compatibility when applied jointly with specifically acting herbicides. Some safeners are themselves herbicidally active. In these cases, the safeners act as antidote or antagonist in the crop plants and thus reduce or even prevent damage to the crop plants. However, in the compositions of the present invention, safeners are generally not required. Therefore, one embodiment of the invention relates to compositions which contain no safener or virtually no safener (i.e. less than 0.1% by weight, based on the total amount of herbicide compound A, herbicide compound B and, if present, herbicide component C. In an other embodiment of the invention, the composition contains at least one safener in an effective amount, which is generally at least 0.1% by weight, in particular at least 0.2 or 0.5% by weight, based on the total amount of herbicide compound A, herbicide compound B and, if present, herbicide component C.

Suitable safeners, which can be used in the compositions according to the present invention are known in the art, e.g. from The Compendium of Pesticide Common Names (http://www.alanwood.net/pesticides/);

Farm Chemicals Handbook 2000 Vol. 86, Meister Publishing Company, 2000;

B. Hock, C. Fedtke, R. R. Schmidt, Herbizide, Georg Thieme Verlag, Stuttgart 1995;

W. H. Ahrens, Herbicide Handbook, 7th Edition, Weed Science Society of America, 1994; and K. K. Hatzios, Herbicide Handbook, Supplement to 7th Edition, Weed Science Society of America, 1998.

Safeners include benoxacor, cyometrinil, cyprosulfamide, dichlormid, dicyclonon, dietholate, fenchlorazole, fenclorim, flurazole, fluxofenim, furilazole, mefenpyr, mephenate, naphthalic anhydride, 2,2,5-trimethyl-3-(dichloracetyl)-1,3-oxazolidine, 4-(dichloroacetyl)-1-oxa-4-azaspiro[4.5]decane and oxabetrinil, as well as thereof agriculturally acceptable salts and, provided they have a carboxyl group, their agriculturally acceptable derivatives. 2,2,5-Trimethyl-3-(dichloracetyl)-1,3-oxazolidine [CAS No. 52836-31-4] is also known under the name R-29148.4-(Dichloroacetyl)-1-oxa-4-azaspiro[4.5]decane [CAS No. 71526-07-03] is also known under the names AD-67 and MON 4660.

As safener, the compositions according to the invention particularly preferably comprise at least one of the compounds selected from the group of benoxacor, cyometrinil, cyprosulfamide, dichlormid, dicyclonon, dietholate, fenchlorazole, fenclorim, flurazole, fluxofenim, furilazole, mefenpyr, mephenate, naphthalic anhydride and oxabetrinil, the salts and esters thereof.

In the compositions of the present invention the relative weight ratio of herbicide compound A, calculated as the free acid (naptalam), to herbicide compound B, calculated as the free acid, is preferably in the range from 1:200 to 200:1, in particular from 1:100 to 100:1 or from 1:50 to 50:1. In a particular preferred embodiment the weight ratio of herbicide compound A, calculated as the free acid, to herbicide compound B, calculated as the free acid, is at most 1:1, in particular at most 1:2 and more preferably at most 1:4, e.g. from 1:200 to 1:1, in particular 1:100 to 1:2 and more preferably from 50:1 to 1:4. However, higher, weight ratios are likewise possible, i.e. the weight ratio of herbicide compound A, calculated as the free acid (naptalam) to herbicide compound B, calculated as the free acid, may be from 1:1 to 200:1, or from 1:1 to 100:1 or from 1:1 to 50:1. Accordingly, in the methods and uses of the invention, naptalam and the herbicide compound B are preferably applied within these weight ratios.

If the compositions of the invention comprise a herbicide component C, the relative weight ratio of herbicide compound A, calculated as the free acid (naptalam), to the total amount of herbicide compounds B and C, calculated as their free acids, is preferably in the range from 1:5000 to 200:1, in particular from 1:1000 to 100:1 or from 1:500 to 50:1. In a particular preferred embodiment the weight ratio of herbicide compound A, calculated as the free acid, to the total amount of herbicide compounds B and C, calculated as their free acids, is at most 1:1, in particular at most 1:2 and more preferably at most 1:4, e.g. from 1:200 to 1:1, in particular 1:100 to 1:2 and more preferably from 50:1 to 1:4. In these compositions, the weight ratio of herbicide compound B to herbicide component C, in each case calculated as their free acids, is from 1:200 to 200:1, in particular from 1:100 to 100:1 or from 1:50 to 50:1. Accordingly, in the methods and uses of the invention, naptalam and the herbicide compounds B and C are preferably applied within these weight ratios.

If the compositions of the invention comprise a safener D, the relative weight ratio of the safener D, calculated, where applicable, as its free acid, to the total amount of herbicide compounds A, B and, if present, C, calculated as their free acids, is preferably in the range from 1:500 to 200:1, in particular from 1:250 to 100:1 or from 1:200 to 50:1. In a particular preferred embodiment the weight ratio of safener D, calculated, where applicable, as its free acid, to the total amount of herbicide compounds A, B and, if present, component C, calculated as their free acids, is at most 1:1, in particular at most 1:2 and more preferably at most 1:4, e.g. from 1:500 to 1:1, in particular 1:250 to 1:2 and more preferably from 200:1 to 1:4. In these compositions, the weight ratio of herbicide compound A to herbicide compound B, or, if the composition comprises a component C, i.e. one or more herbicide compounds C, the weight ratio of the herbicide compound A to the total amount of herbicide compounds B plus C and the weight ratio of the herbicide compound B to herbicide component C, in each case calculated as their free acids, is preferable as given above. Accordingly, in the methods and uses of the invention, naptalam, the safener D and the herbicide compounds B and optionally C are preferably applied within these weight ratios.

According to a particular preferred embodiment (embodiment 1), the composition of the invention comprises naptalam, a salt or an ester thereof, in particular a salt of naptalam, and dicamba, a salt or an ester thereof, in particular a salt of dicamba. In this embodiment, the weight ratio of naptalam to dicamba is as given above for the weight ratio of the herbicide compounds A and B.

The composition of the embodiment 1 may comprise no further herbicide compound C (embodiment 1.0) or may comprise a herbicide component C as defined above, i.e. one or more, e.g. 1, 2, 3 or 4, in particular 1 or 2 further herbicide compounds C, as defined above (embodiments 1.1 to 1.5).

If the compositions of the embodiment 1 contain a herbicide component C, the herbicide component C is preferably herbicide or herbicide mixture, which is selected from the group of synthetic auxins, in particular from the followings compound groups:

c.1 benzoic acid herbicides, which are different from dicamba, in particular tricamba, chloramben or 2,3,6-TBA (2,3,6-trichlorobenzoic acid) and the salts and esters thereof;

c.2 quinolinecarboxylic acid herbicides as mentioned before, in particular quinclorac or quinmerac and the salts and esters thereof as mentioned above;

c.3 pyridinecarboxylic acid herbicides, in particular aminopyralid, clopyralid, picloram, triclopyr or fluoroxypyr and the salts and esters thereof as mentioned above;

c.4 aminocyclopyrachlor, the salts and esters thereof as mentioned above; and c.5 phenoxycarboxylic acid herbicides, e.g. phenoxyacetic acid herbicides such as 2,4-D, 3,4-DA, MCPA, 2,4,5-T, phenoxypropionic acid herbicides such as 2,4-DP (dichlorprop), 2,4-DP-P, 4-CPP, 3,4-DP, fenoprop, MCPP (mecoprop), MCPP-P, and phenoxybutyric acid herbicides such as 4-CPB, 2,4-DB, 3,4-DB, 2,4,5-TB, MCPB, their salts and their esters, in particular one of the following phenoxycarboxylic acid herbicides: 2,4-D, 2,4-DB, 2,4-DP (dichlorprop), 2,4-DP-P, MCPP (mecoprop), MCPP-P, MCPA, MCPB, their salts and their esters; and mixtures thereof, e.g. a mixture of a herbicide of group c.1 with a herbicide of group c.2, a mixture of a herbicide of group c.1 with a herbicide of group c.2, a mixture of a herbicide of group c.1 with a herbicide of group c.3, a mixture of a herbicide of group c.1 with a herbicide of group c.4, a mixture of a herbicide of group c.1 with a herbicide of group c.5, a mixture of a herbicide of group c.2 with a herbicide of group c.3, a mixture of a herbicide of group c.2 with a herbicide of group c.4, a mixture of a herbicide of group c.2 with a herbicide of group c.5 or a, a mixture of a two different herbicides of group c.5.

Particular preferred compositions of the embodiment 1 comprise at least one further, e.g. 1, 2 or 3, herbicide compounds C, which is/are selected from the group c.1, in particular selected from the group consisting of cloramben, tricamba, the salts and the esters thereof (embodiment 1.1).

Further particular preferred compositions of the embodiment 1 comprise at least one, e.g. 1, 2 or 3, further herbicide compounds C, which is/are selected from the group c.2, in particular selected from the group consisting of quinmerac, quinclorac, the salts and the esters thereof as mentioned above (embodiment 1.2).

Further particular preferred compositions of the embodiment 1 comprise at least one, e.g. 1, 2 or 3, further herbicide compounds C, which is/are selected from the group c.3, in particular selected from the group consisting of aminopyralid, clopyralid, picloram, triclopyr, fluoroxypyr, the salts and esters thereof as mentioned above (embodiment 1.3).

Further particular preferred compositions of the embodiment 1 comprise at least one, e.g. 1, 2 or 3, further herbicide compounds C, which is/are selected from aminocyclopyrachlor the salts and esters thereof as mentioned above (embodiment 1.4).

Further particular preferred compositions of the embodiment 1 comprise at least one, e.g. 1, 2 or 3, further herbicide compounds C, which is/are selected from the group c.5, in particular selected from the group consisting of 2,4-D, 2,4-DB, 2,4-DP (dichlorprop), 2,4-DP-P, MCPP (mecoprop), MCPP-P, MCPA, MCPB, the salts and esters thereof as mentioned above (embodiment 1.5). Further particular preferred compositions of the embodiment 1.5 comprise at least two, e.g., further herbicide compounds C, which are selected from the group c.5, in particular selected from the group consisting of 2,4-D, 2,4-DB, 2,4-DP (dichlorprop), 2,4-DP-P, MCPP (mecoprop), MCPP-P, MCPA, MCPB, the salts and esters thereof as mentioned above, e.g. a mixture of 2,4-D with 2,4-DB, a mixture of 2,4-D with 2,4-DP, a mixture of 2,4-D with MCPP, a mixture of 2,4-D with MCPA, a mixture of 2,4-D with MCPB. A particular preferred composition of embodiment 1.5 comprises as the component C a mixture of 2,4-D with mecoprop. Of course, the herbicide compounds C in these mixtures may be present in the form of the salts and esters thereof as mentioned above. In these compositions of embodiment 1.5 the weight ratio of the individual compounds of the group c.5 is usually from 1:100 to 100:1, in particular from 1:20 to 20:1.

Further particular preferred compositions of the embodiment 1 comprise as component C 1 or 2 further herbicide compounds C, which is/are selected from herbicide compounds of the group c.5, in particular selected from the group consisting of 2,4-D, 2,4-DB, 2,4-DP (dichlorprop), 2,4-DP-P, MCPP (mecoprop), MCPP-P, MCPA, MCPB, the salts and esters thereof as mentioned above, and a further herbicide compound which is selected from the herbicide compounds of groups c.1 (different from dicambar or its salts or esters), the herbicide compounds of groups c.2, the herbicide compounds of groups c.3 and the herbicide compounds of groups c.4 (embodiment 1.6). Particular preference is given to those compositions of the embodiment 1.6, which comprise as component C 1 or 2 further herbicide compounds C, which is/are selected from herbicide compounds of the group c.5, in particular selected from the group consisting of 2,4-D, 2,4-DB, 2,4-DP (dichlorprop), 2,4-DP-P, MCPP (mecoprop), MCPP-P, MCPA, MCPB, the salts and esters thereof as mentioned above, and a further herbicide compound which is selected from the herbicide compounds of groups c.2, in particular from quinmerac, quinclorac, the salts and the esters thereof as mentioned above. Particular examples of component C of embodiment 1.6 are mixtures of 2,4-D with quinclorac, 2,4-D with quinmerac, 2,4-DB with quinclorac, 2,4-DB with quinmerac, 2,4-DP with quinclorac, 2,4-DP with quinmerac, MCPP with quinclorac, MCPP with quinmerac, MCPA with quinclorac, MCPA with quinmerac, MCPB with quinclorac and MCPB with quinmerac. In these compositions of embodiment 1.6 the weight ratio of the compounds of the group c.5 to the compounds of the group c.1, c.2, c.3 or c.4 is usually from 1:100 to 100:1, in particular from 1:20 to 20:1.

The compositions of the embodiment 1, in particular the preferred compositions 1.0, 1.1, 1.2, 1.3, 1.4, 1.5 and 1.6, may contain a safener D as defined above, in particular a safener which is selected from the group consisting of benoxacor, cyometrinil, cyprosulfamide, dichlormid, dicyclonon, dietholate, fenchlorazole, fenclorim, flurazole, fluxofenim, furilazole, mefenpyr, mephenate, naphthalic anhydride and oxabetrinil, the salts and esters thereof.

In the compositions of the embodiment 1, in particular in the preferred compositions 1.0, 1.1, 1.2, 1.3, 1.4, 1.5 and 1.6, the weight ratios of herbicide compound A to herbicide compound B, are as defined above. In the compositions 1.1, 1.2, 1.3, 1.4, 1.5 and 1.6, the weight ratios of herbicide compound A to the total amount of herbicide compounds B plus C as well as the weight ratios for the herbicide compound B to the herbicide component C is as defined above. In the compositions of the embodiment 1, in particular in the preferred compositions 1.0, 1.1, 1.2, 1.3, 1.4, 1.5 and 1.6, which contain a safener D, the weight ratio of the safener D to the total amount of herbicide compounds A and B and, if present component C, is as defined above.

According to a further preferred embodiment (embodiment 2), the composition of the invention comprises naptalam, a salt or an ester thereof, in particular a salt of naptalam, and a quinolinecarboxylic acid herbicide as mentioned before, in particular quinclorac or quinmerac or a salt or esters thereof as mentioned above. In this embodiment, the weight ratio of naptalam to quinolinecarboxylic acid herbicide is as given above for the weight ratio of the herbicide compounds A and B.

The composition of the embodiment 2 may comprise no further herbicide compound C (embodiment 2.0) or may comprise one or more, e.g. 1, 2, 3 or 4, in particular 1 or 2, further herbicide compounds C as defined above (embodiments 2.1 to 2.5).

If the compositions of the embodiment 2 contain a herbicide component C, the herbicide compounds of component C is/are preferably a herbicide compound, which is/are selected from the group of synthetic auxins, in particular from the followings compound groups:

c.1 benzoic acid herbicides, which are different from dicamba, in particular tricamba, chloramben or 2,3,6-TBA (2,3,6-trichlorobenzoic acid) and the salts and esters thereof;

c.2 quinolinecarboxylic acid herbicides as mentioned before which are different from the quinolinecarboxylic acid present as herbicide compound B, in particular quinclorac or quinmerac and the salts and esters thereof as mentioned above;

c.3 pyridinecarboxylic acid herbicides, in particular aminopyralid, clopyralid, picloram, triclopyr or fluoroxypyr and the salts and esters thereof as mentioned above;

c.4 aminocyclopyrachlor, the salts and esters thereof as mentioned above; and c.5 phenoxycarboxylic acid herbicides, e.g. phenoxyacetic acid herbicides such as 2,4-D, 3,4-DA, MCPA, 2,4,5-T, phenoxypropionic acid herbicides such as 2,4-DP (dichlorprop), 2,4-DP-P, 4-CPP, 3,4-DP, fenoprop, MCPP (mecoprop), MCPP-P, and phenoxybutyric acid herbicides such as 4-CPB, 2,4-DB, 3,4-DB, 2,4,5-TB, MCPB, their salts and their esters, in particular one of the following phenoxycarboxylic acid herbicides: 2,4-D, 2,4-DB, 2,4-DP (dichlorprop), 2,4-DP-P, MCPP (mecoprop), MCPP-P, MCPA, MCPB, their salts and their esters.

Particular preferred compositions of the embodiment 2 comprise at least one, e.g. 1, 2 or 3, further herbicide compounds C, which is/are selected from the group c.1, in particular selected from the group consisting of cloramben, tricamba, the salts and the esters thereof (embodiment 2.1).

Further particular preferred compositions of the embodiment 2 comprise at least one, e.g. 1, 2 or 3, further herbicide compounds C, which is/are selected from the group c.3, in particular selected from the group consisting of aminopyralid, clopyralid, picloram, triclopyr, fluoroxypyr, the salts and esters thereof as mentioned above (embodiment 2.3).

Further particular preferred compositions of the embodiment 2 comprise at least one further herbicide compound C, which is selected from aminocyclopyrachlor the salts and esters thereof as mentioned above (embodiment 2.4).

Further particular preferred compositions of the embodiment 2 comprise at least one, e.g. 1, 2 or 3, further herbicide compounds C, which is/are selected from the group c.5, in particular selected from the group consisting of 2,4-D, 2,4-DB, 2,4-DP (dichlorprop), 2,4-DP-P, MCPP (mecoprop), MCPP-P, MCPA, MCPB, the salts and esters thereof as mentioned above (embodiment 2.5). Further particular preferred compositions of the embodiment 2.5 comprise at least two, e.g. 2 or 3, further herbicide compounds C, which are selected from the group c.5, in particular selected from the group consisting of 2,4-D, 2,4-DB, 2,4-DP (dichlorprop), 2,4-DP-P, MCPP (mecoprop), MCPP-P, MCPA, MCPB, the salts and esters thereof as mentioned above, e.g. a mixture of 2,4-D with 2,4-DB, a mixture of 2,4-D with 2,4-DP, a mixture of 2,4-D with MCPP, a mixture of 2,4-D with MCPA, a mixture of 2,4-D with MCPB. Of course, the herbicide compounds C in these mixtures may be present in the form of the salts and esters thereof as mentioned above. In these compositions of embodiment 2.5 the weight ratio of the individual compounds of the group c.5 is usually from 1:100 to 100:1, in particular from 1:20 to 20:1.

The compositions of the embodiment 2, in particular the preferred compositions 2.0, 2.1, 2.3, 2.4 and 2.5 may contain a safener D as defined above, in particular a safener which is selected from the group consisting of benoxacor, cyometrinil, cyprosulfamide, dichlormid, dicyclonon, dietholate, fenchlorazole, fenclorim, flurazole, fluxofenim, furilazole, mefenpyr, mephenate, naphthalic anhydride and oxabetrinil, the salts and esters thereof.

In the compositions of the embodiment 2, in particular in the preferred compositions 2.0, 2.1, 2.3, 2.4 and 2.5, the weight ratios of herbicide compound A to herbicide compound B, are as defined above. In the compositions 2.1, 2.3, 2.4 and 2.5 the weight ratios of herbicide compound A to the total amount of herbicide compounds B plus C as well as the weight ratios for the herbicide compound B to the herbicide component C is as defined above. In the compositions of the embodiment 2, in particular in the preferred compositions 2.0, 2.1, 2.3, 2.4 and 2.5, which contain a safener D, the weight ratio of the safener to the total amount of herbicide compounds A and B and, if present component C, is as defined above.

According to a further preferred embodiment (embodiment 3), the composition of the invention comprises naptalam, a salt or an ester thereof, in particular a salt of naptalam, and a pyridinecarboxylic acid herbicide as mentioned before, in particular a pyridinecarboxylic acid herbicide selected from aminopyralid, clopyralid, picloram, triclopyr, fluoroxypyr and the salts and esters thereof as mentioned above. In this embodiment, the weight ratio of naptalam to a pyridinecarboxylic acid herbicide is as given above for the weight ratio of the herbicide compound A and B.

The composition of the embodiment 3 may comprise no further herbicide compound C (embodiment 3.0) or may comprise one or more, e.g. 1, 2, 3 or 4, in particular 1 or 2, further herbicide compounds C as defined above (embodiments 3.1 to 3.5).

If the compositions of the embodiment 3 contain a herbicide component C, the herbicide compound(s) of component C is/are preferably a herbicide, which is/are selected from the group of synthetic auxins, in particular from the followings compound groups:

c.1 benzoic acid herbicides, which are different from dicamba, in particular tricamba, chloramben or 2,3,6-TBA (2,3,6-trichlorobenzoic acid) and the salts and esters thereof;

c.3 pyridinecarboxylic acid herbicides which are different from the pyridinecarboxylic herbicide which is already present in the composition as herbicide compound B, in particular aminopyralid, clopyralid, picloram, triclopyr or fluoroxypyr and the salts and esters thereof as mentioned above;

c.4 aminocyclopyrachlor, the salts and esters thereof as mentioned above; and c.5 phenoxycarboxylic acid herbicides, e.g. phenoxyacetic acid herbicides such as 2,4-D, 3,4-DA, MCPA, 2,4,5-T, phenoxypropionic acid herbicides such as 2,4-DP (dichlorprop), 2,4-DP-P, 4-CPP, 3,4-DP, fenoprop, MCPP (mecoprop), MCPP-P, and phenoxybutyric acid herbicides such as 4-CPB, 2,4-DB, 3,4-DB, 2,4,5-TB, MCPB, their salts and their esters, in particular one of the following phenoxycarboxylic acid herbicides: 2,4-D, 2,4-DB, 2,4-DP (dichlorprop), 2,4-DP-P, MCPP (mecoprop), MCPP-P, MCPA, MCPB, their salts and their esters.

Particular preferred compositions of the embodiment 3 comprise at least one, e.g. 1, 2 or 3, further herbicide compounds C, which is/are selected from the group c.1, in particular selected from the group consisting of cloramben, tricamba, the salts and the esters thereof (embodiment 3.1).

Further particular preferred compositions of the embodiment 3 comprise at least one, e.g. 1, 2 or 3, further herbicide compounds C, which is/are selected from the group c.3, in particular selected from the group consisting of aminopyralid, clopyralid, picloram, triclopyr, fluoroxypyr, the salts and esters thereof as mentioned above (embodiment 3.3), provided that the compound is different from the herbicide compound B.

Further particular preferred compositions of the embodiment 3 comprise at least one further herbicide compound C, which is selected from aminocyclopyrachlor the salts and esters thereof as mentioned above (embodiment 3.4).

Further particular preferred compositions of the embodiment 3 comprise at least one, e.g. 1, 2 or 3, further herbicide compounds C, which is/are selected from the group c.5, in particular selected from the group consisting of 2,4-D, 2,4-DB, 2,4-DP (dichlorprop), 2,4-DP-P, MCPP (mecoprop), MCPP-P, MCPA, MCPB, the salts and esters thereof as mentioned above (embodiment 3.5). Further particular preferred compositions of the embodiment 3.5 comprise at least two, e.g. 2 or 3, further herbicide compounds C, which are selected from the group c.5, in particular selected from the group consisting of 2,4-D, 2,4-DB, 2,4-DP (dichlorprop), 2,4-DP-P, MCPP (mecoprop), MCPP-P, MCPA, MCPB, the salts and esters thereof as mentioned above, e.g. a mixture of 2,4-D with 2,4-DB, a mixture of 2,4-D with 2,4-DP, a mixture of 2,4-D with MCPP, a mixture of 2,4-D with MCPA, a mixture of 2,4-D with MCPB. Of course, the herbicide compounds C in these mixtures may be present in the form of the salts and esters thereof as mentioned above. In these compositions of embodiment 3.5 the weight ratio of the individual compounds of the group c.5 is usually from 1:100 to 100:1, in particular from 1:20 to 20:1.

The compositions of the embodiment 3, in particular the preferred compositions 3.0, 3.1, 3.3, 3.4 and 3.5 may contain a safener D as defined above, in particular a safener which is selected from the group consisting of benoxacor, cyometrinil, cyprosulfamide, dichlormid, dicyclonon, dietholate, fenchlorazole, fenclorim, flurazole, fluxofenim, furilazole, mefenpyr, mephenate, naphthalic anhydride and oxabetrinil, the salts and esters thereof.

In the compositions of the embodiment 3, in particular in the preferred compositions 3.0, 3.1, 3.3, 3.4 and 3.5, the weight ratios of herbicide compound A to herbicide compound B, are as defined above. In the compositions 3.1, 3.3, 3.4 and 3.5 the weight ratios of herbicide compound A to the total amount of herbicide compounds B plus C as well as the weight ratios for the herbicide compound B to the herbicide compound C is as defined above. In the compositions of the embodiment 3, in particular in the preferred compositions 3.0, 3.1, 3.3, 3.4 and 3.5, which contain a safener D, the weight ratio of the safener to the total amount of herbicide compounds A and B and, if present component C, is as defined above.

According to a further preferred embodiment (embodiment 4), the composition of the invention comprises naptalam, a salt or an ester thereof, in particular a salt of naptalam, and aminocyclopyrachlor, the salts and esters thereof as mentioned above. In this embodiment, the weight ratio of naptalam to aminocyclopyrachlor is as given above for the weight ratio of the herbicide compounds A and B.

The composition of the embodiment 4 may comprise no further herbicide compound C (embodiment 4.0) or may comprise one or more, e.g. 1, 2, 3 or 4, in particular 1 or 2, further herbicide compounds C as defined above (embodiments 4.1 to 4.5).

If the compositions of the embodiment 4 contain a herbicide component C, the herbicide compound(s) of component C is/are preferably a herbicide, which is/are selected from the group of synthetic auxins, in particular from the followings compound groups:

c.1 benzoic acid herbicides, which are different from dicamba, in particular tricamba, chloramben or 2,3,6-TBA (2,3,6-trichlorobenzoic acid) and the salts and esters thereof;

c.2 quinolinecarboxylic acid herbicides as mentioned before, in particular quinclorac or quinmerac and the salts and esters thereof as mentioned above;

c.3 pyridinecarboxylic acid herbicides, in particular aminopyralid, clopyralid, picloram, triclopyr or fluoroxypyr and the salts and esters thereof as mentioned above;

c.5 phenoxycarboxylic acid herbicides, e.g. phenoxyacetic acid herbicides such as 2,4-D, 3,4-DA, MCPA, 2,4,5-T, phenoxypropionic acid herbicides such as 2,4-DP (dichlorprop), 2,4-DP-P, 4-CPP, 3,4-DP, fenoprop, MCPP (mecoprop), MCPP-P, and phenoxybutyric acid herbicides such as 4-CPB, 2,4-DB, 3,4-DB, 2,4,5-TB, MCPB, their salts and their esters, in particular one of the following phenoxycarboxylic acid herbicides: 2,4-D, 2,4-DB, 2,4-DP (dichlorprop), 2,4-DP-P, MCPP (mecoprop), MCPP-P, MCPA, MCPB, their salts and their esters.

Particular preferred compositions of the embodiment 4 comprise at least one, e.g. 1, 2 or 3, further herbicide compounds C, which is/are selected from the group c.1, in particular selected from the group consisting of cloramben, tricamba, the salts and the esters thereof (embodiment 4.1).

Further particular preferred compositions of the embodiment 4 comprise at least one, e.g. 1, 2 or 3, further herbicide compounds C, which is/are selected from the group c.2, in particular selected from the group consisting of quinmerac, quinclorac, the salts and the esters thereof as mentioned above (embodiment 4.2).

Further particular preferred compositions of the embodiment 4 comprise at least one, e.g. 1, 2 or 3, further herbicide compounds C, which is/are selected from the group c.3, in particular selected from the group consisting of aminopyralid, clopyralid, picloram, triclopyr, fluoroxypyr, the salts and esters thereof as mentioned above (embodiment 4.3).

Further particular preferred compositions of the embodiment 4 comprise at least one, e.g. 1, 2 or 3, further herbicide compounds C, which is/are selected from the group c.5, in particular selected from the group consisting of 2,4-D, 2,4-DB, 2,4-DP (dichlorprop), 2,4-DP-P, MCPP (mecoprop), MCPP-P, MCPA, MCPB, the salts and esters thereof as mentioned above (embodiment 4.5). Further particular preferred compositions of the embodiment 4.5 comprise at least two, e.g. 2 or 3, further herbicide compounds C, which are selected from the group c.5, in particular selected from the group consisting of 2,4-D, 2,4-DB, 2,4-DP (dichlorprop), 2,4-DP-P, MCPP (mecoprop), MCPP-P, MCPA, MCPB, the salts and esters thereof as mentioned above, e.g. a mixture of 2,4-D with 2,4-DB, a mixture of 2,4-D with 2,4-DP, a mixture of 2,4-D with MCPP, a mixture of 2,4-D with MCPA, a mixture of 2,4-D with MCPB. Of course, the herbicide compounds C in these mixtures may be present in the form of the salts and esters thereof as mentioned above. In these compositions of embodiment 4.5 the weight ratio of the individual compounds of the group c.5 is usually from 1:100 to 100:1, in particular from 1:20 to 20:1.

The compositions of the embodiment 4, in particular the preferred compositions 4.0, 4.1, 4.2, 4.3 and 4.5 may contain a safener D as defined above, in particular a safener which is selected from the group consisting of benoxacor, cyometrinil, cyprosulfamide, dichlormid, dicyclonon, dietholate, fenchlorazole, fenclorim, flurazole, fluxofenim, furilazole, mefenpyr, mephenate, naphthalic anhydride and oxabetrinil, the salts and esters thereof.

In the compositions of the embodiment 2, in particular in the preferred compositions 4.0, 4.1, 4.2, 4.3 and 4.5, the weight ratios of herbicide compound A to herbicide compound B, are as defined above. In the compositions 4.1, 4.2, 4.3 and 4.5 the weight ratios of herbicide compound A to the total amount of herbicide compounds B plus C as well as the weight ratios for the herbicide compound B to the herbicide compound C is as defined above. In the compositions of the embodiment 4, in particular in the preferred compositions 4.0, 4.1, 4.2, 4.3 and 4.5, which contain a safener D, the weight ratio of the safener to the total amount of herbicide compounds A and B and, if present component C, is as defined above.

Examples of particular preferred compositions of the invention are given in the following table A. In the compositions of table A, the herbicide compound A is naptalam or a suitable salt thereof. In the compositions of table A, the weight ratios of herbicide compound A to herbicide compound B, are as defined above. In the compositions of table A which contain a herbicide compound C, the weight ratios of herbicide compound A to the total amount of herbicide compounds B+C as well as the weight ratios for the herbicide compound B to the herbicide compound C is as defined above.

TABLE A

| Embodiment | Herbicide B* | Herbicide C* |
|---|---|---|
| 1.0.1 | dicamba | |
| 1.1.1 | dicamba | chloramben |
| 1.1.2 | dicamba | tricamba |
| 1.2.1 | dicamba | quinmerac |
| 1.2.2 | dicamba | quinclorac |
| 1.3.1 | dicamba | aminopyralid |
| 1.3.2 | dicamba | clopyralid |
| 1.3.3 | dicamba | picloram |
| 1.3.4 | dicamba | triclopyr |
| 1.3.5 | dicamba | fluroxypyr |
| 1.4.1 | dicamba | aminocyclopyrachlor |
| 1.5.1 | dicamba | 2,4-D |
| 1.5.2 | dicamba | 2,4-DP |
| 1.5.3 | dicamba | 2,4-DP-P |
| 1.5.4 | dicamba | MCPP |
| 1.5.5 | dicamba | MCPP-P |
| 1.5.6 | dicamba | MCPA |
| 1.5.7 | dicamba | MCPB |
| 1.5.8 | dicamba | 2,4-DB |
| 1.5.9 | dicamba | 2,4-D + MCPP |
| 1.5.10 | dicamba | 2,4-D + MCPP-P |
| 1.5.11 | dicamba | 2,4-D + MCPA |
| 1.5.12 | dicamba | 2,4-D + MCPB |
| 1.5.13 | dicamba | 2,4-DP + MCPP |
| 1.5.14 | dicamba | 2,4-DP + MCPP-P |
| 1.5.15 | dicamba | 2,4-DP + MCPA |
| 1.5.16 | dicamba | 2,4-DP + MCPB |
| 1.5.17 | dicamba | 2,4-DB + MCPP |
| 1.5.18 | dicamba | 2,4-DB + MCPP-P |
| 1.5.19 | dicamba | 2,4-DB + MCPA |
| 1.5.20 | dicamba | 2,4-DB + MCPB |
| 1.5.21 | dicamba | 2,4-DP-P + MCPP |
| 1.5.22 | dicamba | 2,4-DP-P + MCPP-P |
| 1.5.23 | dicamba | 2,4-DP-P + MCPA |
| 1.5.24 | dicamba | 2,4-DP-P + MCPB |
| 1.5.25 | dicamba | 2,4-D + 2,4-DB |
| 1.5.26 | dicamba | 2,4-D + 2,4-DP |
| 1.5.27 | dicamba | 2,4-D + 2,4-DP-P |
| 1.5.28 | dicamba | MCPP + MCPA |
| 1.5.29 | dicamba | MCPP + MCPB |
| 1.5.30 | dicamba | MCPP-P + MCPA |
| 1.5.31 | dicamba | MCPP-P + MCPB |
| 1.5.32 | dicamba | MCPA + MCPB |
| 1.6.1 | dicamba | quinmerac + 2,4-D |
| 1.6.2 | dicamba | quinmerac + 2,4-DB |
| 1.6.3 | dicamba | quinmerac + 2,4-DP |
| 1.6.4 | dicamba | quinmerac + 2,4-DP-P |
| 1.6.5 | dicamba | quinmerac + MCPP |
| 1.6.6 | dicamba | quinmerac + MCPP-P |
| 1.6.7 | dicamba | quinmerac + MCPA |
| 1.6.8 | dicamba | quinmerac + MCPB |
| 1.6.9 | dicamba | quinclorac + 2,4-D |
| 1.6.10 | dicamba | quinclorac + 2,4-DB |
| 1.6.11 | dicamba | quinclorac + 2,4-DP |
| 1.6.12 | dicamba | quinclorac + 2,4-DP-P |
| 1.6.13 | dicamba | quinclorac + MCPP |
| 1.6.14 | dicamba | quinclorac + MCPP-P |
| 1.6.15 | dicamba | quinclorac + MCPA |
| 1.6.16 | dicamba | quinclorac + MCPB |
| 2.0.1 | quinmerac | |
| 2.0.2 | quinclorac | |
| 2.1.1 | quinmerac | chloramben |
| 2.1.2 | quinmerac | tricamba |
| 2.1.3 | quinclorac | chloramben |
| 2.1.4 | quinclorac | tricamba |
| 2.3.1 | quinmerac | aminopyralid |
| 2.3.2 | quinmerac | clopyralid |
| 2.3.3 | quinmerac | picloram |
| 2.3.4 | quinmerac | triclopyr |
| 2.3.5 | quinmerac | fluroxypyr |
| 2.3.6 | quinclorac | aminopyralid |
| 2.3.7 | quinclorac | clopyralid |
| 2.3.8 | quinclorac | picloram |
| 2.3.9 | quinclorac | triclopyr |
| 2.3.10 | quinclorac | fluroxypyr |
| 2.4.1 | quinmerac | aminocyclopyrachlor |
| 2.4.2 | quinclorac | aminocyclopyrachlor |
| 2.5.1 | quinmerac | 2,4-D |

TABLE A-continued

| Embodiment | Herbicide B* | Herbicide C* |
|---|---|---|
| 2.5.2 | quinmerac | 2,4-DP |
| 2.5.3 | quinmerac | 2,4-DP-P |
| 2.5.4 | quinmerac | MCPP |
| 2.5.5 | quinmerac | MCPP-P |
| 2.5.6 | quinmerac | MCPA |
| 2.5.7 | quinmerac | MCPB |
| 2.5.8 | quinclorac | 2,4-D |
| 2.5.9 | quinclorac | 2,4-DP |
| 2.5.10 | quinclorac | 2,4-DP-P |
| 2.5.11 | quinclorac | MCPP |
| 2.5.12 | quinclorac | MCPP-P |
| 2.5.13 | quinclorac | MCPA |
| 2.5.14 | quinclorac | MCPB |
| 2.5.15 | quinmerac | 2,4-DB |
| 2.5.16 | quinclorac | 2,4-DB |
| 3.0.1 | aminopyralid | |
| 3.0.2 | clopyralid | |
| 3.0.3 | picloram | |
| 3.0.4 | triclopyr | |
| 3.0.5 | fluroxypyr | |
| 3.1.1 | aminopyralid | chloramben |
| 3.1.2 | aminopyralid | tricamba |
| 3.1.3 | clopyralid | chloramben |
| 3.1.4 | clopyralid | tricamba |
| 3.1.5 | picloram | chloramben |
| 3.1.6 | picloram | tricamba |
| 3.1.7 | triclopyr | chloramben |
| 3.1.8 | triclopyr | tricamba |
| 3.1.9 | fluroxypyr | chloramben |
| 3.1.10 | fluroxypyr | tricamba |
| 3.4.1 | aminopyralid | aminocyclopyrachlor |
| 3.4.2 | clopyralid | aminocyclopyrachlor |
| 3.4.3 | picloram | aminocyclopyrachlor |
| 3.4.4 | triclopyr | aminocyclopyrachlor |
| 3.4.5 | fluroxypyr | aminocyclopyrachlor |
| 3.5.1 | aminopyralid | 2,4-D |
| 3.5.2 | aminopyralid | 2,4-DP |
| 3.5.3 | aminopyralid | 2,4-DP-P |
| 3.5.4 | aminopyralid | MCPP |
| 3.5.5 | aminopyralid | MCPP-P |
| 3.5.6 | aminopyralid | MCPA |
| 3.5.7 | aminopyralid | MCPB |
| 3.5.8 | clopyralid | 2,4-D |
| 3.5.9 | clopyralid | 2,4-DP |
| 3.5.10 | clopyralid | 2,4-DP-P |
| 3.5.11 | clopyralid | MCPP |
| 3.5.12 | clopyralid | MCPP-P |
| 3.5.13 | clopyralid | MCPA |
| 3.5.14 | clopyralid | MCPB |
| 3.5.15 | picloram | 2,4-D |
| 3.5.16 | picloram | 2,4-DP |
| 3.5.17 | picloram | 2,4-DP-P |
| 3.5.18 | picloram | MCPP |
| 3.5.19 | picloram | MCPP-P |
| 3.5.20 | picloram | MCPA |
| 3.5.21 | picloram | MCPB |
| 3.5.22 | triclopyr | 2,4-D |
| 3.5.23 | triclopyr | 2,4-DP |
| 3.5.24 | triclopyr | 2,4-DP-P |
| 3.5.25 | triclopyr | MCPP |
| 3.5.26 | triclopyr | MCPP-P |
| 3.5.27 | triclopyr | MCPA |
| 3.5.28 | triclopyr | MCPB |
| 3.5.29 | fluroxypyr | 2,4-D |
| 3.5.30 | fluroxypyr | 2,4-DP |
| 3.5.31 | fluroxypyr | 2,4-DP-P |
| 3.5.32 | fluroxypyr | MCPP |
| 3.5.33 | fluroxypyr | MCPP-P |
| 3.5.34 | fluroxypyr | MCPA |
| 3.5.35 | fluroxypyr | MCPB |
| 3.5.36 | aminopyralid | 2,4-DB |
| 3.5.37 | clopyralid | 2,4-DB |
| 3.5.38 | picloram | 2,4-DB |
| 3.5.39 | triclopyr | 2,4-DB |
| 3.5.40 | fluroxypyr | 2,4-DB |
| 4.0.1 | aminocyclopyrachlor | |
| 4.1.1 | aminocyclopyrachlor | chloramben |
| 4.1.2 | aminocyclopyrachlor | tricamba |
| 4.5.1 | aminocyclopyrachlor | 2,4-D |
| 4.5.2 | aminocyclopyrachlor | 2,4-DP |
| 4.5.3 | aminocyclopyrachlor | 2,4-DP-P |
| 4.5.4 | aminocyclopyrachlor | MCPP |
| 4.5.5 | aminocyclopyrachlor | MCPP-P |
| 4.5.6 | aminocyclopyrachlor | MCPA |
| 4.5.7 | aminocyclopyrachlor | MCPB |
| 4.5.8 | aminocyclopyrachlor | 2,4-DB |

*In the compositions of table A, the free acid is given. Likewise a salt or an ester of the herbicide compounds A, B or C.

The compositions of table A may also contain a safener D as described above, in particular a safener D of the group consisting of benoxacor, cyometrinil, cyprosulfamide, dichlormid, dicyclonon, dietholate, fenchlorazole, fenclorim, flurazole, fluxofenim, furilazole, mefenpyr, mephenate, naphthalic anhydride and oxabetrinil, the salts and esters thereof. In the compositions, which comprise a safener D, the weight ratio of the safener to the total amount of herbicide compounds A and B and, if present C, is as defined above.

The compositions of the present invention are suitable for controlling a large number of dicotyledonous weeds, in particular broadleaf weeds including *Polygonum* species such as wild buckwheat (*Polygonum convolvolus*), *Amaranthus* species such as pigweed (*Amaranthus retroflexus*), *Chenopodium* species such as common lambsquarters (*Chenopodium album* L.), *Sida* species such as prickly sida (*Sida spinosa* L.), *Ambrosia* species such as common ragweed (*Ambrosia artemisiifolia*), *Acanthospermum* species, *Anthemis* species, *Atriplex* species, *Cirsium* species, *Convolvulus* species, *Conyza* species, such as horseweed (*Conyza canadensis*), *Cassia* species, *Commelina* species, *Datura* species, *Euphorbia* species, *Geranium* species, *Galinsoga* species, morning-glory (*Ipomoea* species), *Lamium* species, *Malva* species, *Matricaria* species, *Sysimbrium* species, *Solanum* species, *Xanthium* species, *Veronica* species, *Viola* species, common chickweed (*Stellaria media*), velvetleaf (*Abutilon theophrasti*), Hemp sesbania (*Sesbania exaltata* Cory), *Anoda cristata, Bidens pilosa, Brassica kaber, Capsella bursa-pastoris, Centaurea cyanus, Galeopsis tetrahit, Galium aparine, Helianthus annuus, Desmodium tortuosum, Kochia scoparia, Mercurialis annua, Myosotis arvensis, Papaver rhoeas, Raphanus raphanistrum, Salsola kali, Sinapis arvensis, Sonchus arvensis, Thlaspi arvense, Tagetes minuta, Richardia brasiliensis*, and the like.

The compositions of the present invention can also be used in forestry, e.g. for site preparation but also for combating undesirable vegetation in forests.

The compositions of the present invention are in particular suitable for combating/controlling undesired vegetation in
    grain crops, including in particular
        cereals such as wheat, and wheat like crops, rye, triticale and barley,
        maize,
        sorghum,
        rice, and
        sugarcane,
    pulse crops such as pea, bean and lentils,
    oilseed crops such as canola, oilseed rape and sunflower,
    forage crops such as alfalfa and clover,
    cotton and
    soybean.

The compositions of the present invention are in particular suitable for combating/controlling undesired vegetation in non-crop areas, in particular in turf, pasture, fallow or rangeland. The compositions of the present invention are also particularly suitable for rights-of-way applications.

If not stated otherwise, the compositions of the invention are suitable for application in any variety of the aforementioned crop plants.

The compositions according to the invention can also be used in crop plants which are resistant to one or more herbicides owing to genetic engineering or breeding, which are resistant to one or more pathogens such as plant pathogenous fungi owing to genetic engineering or breeding, or which are resistant to attack by insects owing to genetic engineering or breeding. Suitable are for example crop plants, preferably corn (maize), sorghum, wheat, sunflower, rice, canola, oilseed rape, soybeans, cotton, alfalfa, clover, and sugarcane which are resistant to synthetic auxins, or crop plants which, owing to introduction of the gene for Bt toxin by genetic modification, are resistant to attack by certain insects.

The compositions of this embodiment can preferably be used in crops which are tolerant and/or resistant to the action of at least one of the herbicide compounds B and/or C, more preferably in crops which are tolerant and/or are resistant to the action of synthetic auxin herbicides of the groups b.1, b.2, b.3, b.4, c.1 or c.5, in particular resistant and/or tolerant to the action of dicamba and/or phenoxycarboxylic acid herbicides. The resistance to said herbicides may be achieved by conventional breeding and/or by genetic engineering methods. Crops which may be resistant to auxin herbicides include in particular crops of soybeans, cotton, corn, sorghum, wheat, rye, barley, triticale, alfalfa, clover, sugarcane and rice.

The compositions of the present invention can be applied in a conventional manner by a skilled personal familiar with the techniques of applying herbicides. Suitable techniques include spraying, atomizing, dusting, spreading or watering. The type of application depends on the intended purpose in a well known manner; in any case, they should ensure the finest possible distribution of the active ingredients according to the invention.

The compositions can be applied pre- or post-emergence, i.e. before, during and/or after emergence of the undesirable plants. When the compositions are used in crops, they can be applied after seeding and before or after the emergence of the crop plants. The compositions invention can, however, also be applied prior to seeding of the crop plants.

It is a particular benefit of the compositions according to the invention that they have a very good post-emergence herbicide activity, i.e. they show a good herbicidal activity against emerged undesirable plants. Thus, in a preferred embodiment of invention, the compositions are applied postemergence, i.e. during and/or after, the emergence of the undesirable plants. It is particularly advantageous to apply the mixtures according to the invention post emergent when the undesirable plant starts with leaf development up to flowering. Since the compositions of the present invention show good crop tolerance, even when the crop has already emerged, they can be applied after seeding of the crop plants and in particular during or after the emergence of the crop plants.

In any case herbicide compound A, and the compound B and, if desired, herbicide component C and/or safener D, can be applied simultaneously or in succession.

The compositions are applied to the plants mainly by spraying, in particular foliar spraying. Application can be carried out by customary spraying techniques using, for example, water as carrier and spray liquor rates of 10 to 2000 l/ha or 50 to 1000 l/ha (for example from 100 to 500 l/ha). Application of the herbicidal compositions by the low-volume and the ultra-low-volume method is possible, as is their application in the form of microgranules.

If the active ingredients are less well tolerated by certain crop plants, application techniques may be used in which the herbicidal compositions are sprayed, with the aid of the spray apparatus, in such a way that they come into as little contact, if any, with the leaves of the sensitive crop plants while reaching the leaves of undesirable plants which grow underneath, or the bare soil (post-directed, lay-by).

In the case of a post-emergence treatment of the plants, the herbicidal mixtures or compositions according to the invention are preferably applied by foliar application. Application may be effected, for example, by usual spraying techniques with water as the carrier, using amounts of spray mixture of approx. 50 to 1000 l/ha.

In the method of the invention, the application rate of the herbicide compound A, calculated as N-1-naphthylphthalamic acid, is from generally from 1 to 1000 g/ha, in particular from 10 to 500 g/ha and especially from 15 to 280 g/ha.

In the method of the invention, the application rate of the herbicide compound B, calculated as the acid, is generally from 5 to 2500 g/ha, frequently from 10 to 2500 g/ha, in particular from 20 to 2000 g/ha and especially from 30 to 1500 g/ha.

In the method of the invention, the application rate of the herbicide compound C, calculated as the acid, is generally from 5 to 3000 g/ha, frequently from 10 to 3000 g/ha, in particular from 20 to 2000 g/ha and especially from 30 to 1500 g/ha.

The rate of application of the benzoic acid herbicides is usually from 10 to 2000 g/ha, as a rule from 15 to 1500 g/ha, preferably from 20 to 1120 g/ha, of active substance (a.s.).

The rate of application of the quinolinecarboxylic acid herbicide is usually from 10 to 1500 g/ha, as a rule from 15 to 1000 g/ha, preferably from 20 to 750 g/ha, of active substance (a.s.).

The rate of application of the pyridinecarboxylic acid herbicide is usually from 10 to 2000 g/ha, preferably from 15 to 1500 g/ha, in particular from 20 to 1200 g/ha of active substance (a.s.).

The rate of application of aminocyclopyrachlor is usually from 5 to 1500 g/ha, frequently from 10 to 1500 g/ha, as a rule from 15 to 1000 g/ha, preferably from 20 to 750 g/ha, of active substance (a.s.).

The rate of application of the phenoxycarboxylic acid herbicide is usually from 10 to 3000 g/ha, as a rule from 20 to 2000 g/ha, preferably from 30 to 1500 g/ha, of active substance (a.s.).

The present invention also relates to formulations of the compositions according to the present invention. The formulations contain, besides the composition, at least one organic or inorganic carrier material. The formulations may also contain, if desired, one or more surfactants and, if desired, one or more further auxiliaries customary for crop protection compositions.

The formulation may be in the form of a single package formulation containing both the herbicide compound A and the herbicide compound B, and, if desired, herbicide component C and/or safener, together with liquid and/or solid carrier materials, and, if desired, one or more surfactants and, if desired, one or more further auxiliaries customary for crop protection compositions. The formulation may be in the form of a two package formulation, wherein one package contains a formulation of herbicide compound A while the other package contains a formulation of the herbicide compound B and, if desired, herbicide component C and/or a safener D, and wherein both formulations contain at least one carrier material, if desired, one or more surfactants and, if desired, one or more further auxiliaries customary for crop protection compositions. In the case of two package formulations the formulation containing the herbicide compound A and the formulation containing the herbicide compound B and, if desired, herbicide component C and/or a safener D, are mixed prior to application. Preferably the mixing is performed as a tank mix, i.e. the formulations are mixed immediately prior or upon dilution with water.

In the formulation of the present invention the active ingredients, i.e. herbicide compound A, herbicide compound B and optional further actives (e.g. herbicide component C and/or safener D) are present in suspended, emulsified or dissolved form. The formulation according to the invention can be in the form of aqueous solutions, powders, suspensions, also highly-concentrated aqueous, oily or other suspensions or dispersions, aqueous emulsions, aqueous microemulsions, aqueous suspo-emulsions, oil dispersions, pastes, dusts, materials for spreading or granules.

Depending on the formulation type, they comprise one or more liquid or solid carriers, if appropriate surfactants (such as dispersants, protective colloids, emulsifiers, wetting agents and tackifiers), and if appropriate further auxiliaries which are customary for formulating crop protection products. The person skilled in the art is sufficiently familiar with the recipes for such formulations. Further auxiliaries include e.g. organic and inorganic thickeners, bactericides, antifreeze agents, antifoams, colorants and, for seed formulations, adhesives.

Suitable carriers include liquid and solid carriers. Liquid carriers include e.g. non-aqueous solvents such as cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone, and water as well as mixtures thereof. Solid carriers include e.g. mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas, and products of vegetable origin such as cereal meal, tree bark meal, wood meal and nutshell meal, cellulose powders, or other solid carriers.

Suitable surfactants (adjuvants, wetting agents, tackifiers, dispersants and also emulsifiers) are the alkali metal salts, alkaline earth metal salts and ammonium salts of aromatic sulfonic acids, for example lignosulfonic acids (e.g. Borrespers-types, Borregaard), phenolsulfonic acids, naphthalenesulfonic acids (Morwet types, Akzo Nobel) and dibutylnaphthalenesulfonic acid (Nekal types, BASF SE), and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors and proteins, denaturated proteins, polysaccharides (e.g. methylcellulose), hydrophobically modified starches, polyvinyl alcohol (Mowiol types Clariant), polycarboxylates (BASF SE, Sokalan types), polyalkoxylates, polyvinylamine (BASF SE, Lupamine types), polyethyleneimine (BASF SE, Lupasol types), polyvinylpyrrolidone and copolymers thereof.

Examples of thickeners (i.e. compounds which impart to the formulation modified flow properties, i.e. high viscosity in the state of rest and low viscosity in motion) are polysaccharides, such as xanthan gum (Kelzan® from Kelco), Rhodopol® 23 (Rhone Poulenc) or Veegum® (from R.T. Vanderbilt), and also organic and inorganic sheet minerals, such as Attaclay® (from Engelhardt).

Examples of antifoams are silicone emulsions (such as, for example, Silikon® SRE, Wacker or Rhodorsil® from Rhodia), long-chain alcohols, fatty acids, salts of fatty acids, organofluorine compounds and mixtures thereof.

Bactericides can be added for stabilizing the aqueous herbicidal formulations. Examples of bactericides are bactericides based on dichlorophen and benzyl alcohol hemiformal (Proxel® from ICI or Acticide® RS from Thor Chemie and Kathon® MK from Rohm & Haas), and also isothiazolinone derivates, such as alkylisothiazolinones and benzisothiazolinones (Acticide MBS from Thor Chemie).

Examples of antifreeze agents are ethylene glycol, propylene glycol, urea or glycerol.

Examples of colorants are both sparingly water-soluble pigments and water-soluble dyes. Examples which may be mentioned are the dyes known under the names Rhodamin B, C.I. Pigment Red 112 and C.I. Solvent Red 1, and also pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of adhesives are polyvinylpyrrolidone, polyvinyl acetate, polyvinyl alcohol and tylose.

To prepare emulsions, pastes or oil dispersions, the active the components, as such or dissolved in an oil or solvent, can be homogenized in water by means of wetting agent, tackifier, dispersant or emulsifier. Alternatively, it is possible to prepare concentrates consisting of active substance, wetting agent, tackifier, dispersant or emulsifier and, if desired, solvent or oil, and these concentrates are suitable for dilution with water.

Powders, materials for spreading and dusts can be prepared by mixing or concomitant grinding of the active the components a) and b) and optionally safener c) with a solid carrier.

Granules, e.g. coated granules, impregnated granules and homogeneous granules, can be prepared by binding the active ingredients to solid carriers.

The formulations of the invention comprise a herbicidally effective amount of the composition of the present invention. The concentrations of the active the active ingredients in the formulations can be varied within wide ranges. In general, the formulations comprise from 1 to 98% by weight, preferably 10 to 60% by weight, of active ingredients (sum of naptalam, herbicide compound B and optionally further active compounds). The active ingredients are employed in a purity of from 90% to 100%, preferably 95% to 100% (according to NMR spectrum).

The active herbicide compounds A and B as well as the compositions according to the invention can, for example, be formulated as follows:

1. Products for Dilution with Water
A Water-Soluble Concentrates 10 parts by weight of active compound (or composition) are dissolved in 90 parts by weight of water or a water-soluble solvent. As an alternative, wetters or other adjuvants are added. The active compound dissolves upon dilution with water. This gives a formulation with an active compound content of 10% by weight.

B Dispersible Concentrates 20 parts by weight of active compound (or composition) are dissolved in 70 parts by weight of cyclohexanone with addition of 10 parts by weight of a dispersant, for example polyvinylpyrrolidone. Dilution with water gives a dispersion. The active compound content is 20% by weight.

C Emulsifiable Concentrates 15 parts by weight of active compound (or composition) are dissolved in 75 parts by weight of an organic solvent (eg. alkylaromatics) with addition of calcium dodecylbenzenesulfonate and castor oil ethoxylate (in each case 5 parts by weight). Dilution with water gives an emulsion. The formulation has an active compound content of 15% by weight.

D Emulsions 25 parts by weight of active compound (or composition) are dissolved in 35 parts by weight of an organic solvent (eg. alkylaromatics) with addition of calcium dodecylbenzenesulfonate and castor oil ethoxylate (in each case 5 parts by weight). This mixture is introduced into 30 parts by weight of water by means of an emulsifier (Ultraturrax) and made into a homogeneous emulsion. Dilution with water gives an emulsion. The formulation has an active compound content of 25% by weight.

E Suspensions

In an agitated ball mill, 20 parts by weight of active compound (or composition) are comminuted with addition of 10 parts by weight of dispersants and wetters and 70 parts by weight of water or an organic solvent to give a fine active compound suspension. Dilution with water gives a stable suspension of the active compound. The active compound content in the formulation is 20% by weight.

F Water-Dispersible Granules and Water-Soluble Granules 50 parts by weight of active compound (or composition) are ground finely with addition of 50 parts by weight of dispersants and wetters and made into water-dispersible or water-soluble granules by means of technical appliances (for example extrusion, spray tower, fluidized bed). Dilution with water gives a stable dispersion or solution of the active compound. The formulation has an active compound content of 50% by weight.

G Water-Dispersible Powders and Water-Soluble Powders 75 parts by weight of active compound (or composition) are ground in a rotor-stator mill with addition of 25 parts by weight of dispersants, wetters and silica gel. Dilution with water gives a stable dispersion or solution of the active compound. The active compound content of the formulation is 75% by weight.

H Gel Formulations

In a ball mill, 20 parts by weight of active compound (or composition), 10 parts by weight of dispersant, 1 part by weight of gelling agent and 70 parts by weight of water or of an organic solvent are mixed to give a fine suspension. Dilution with water gives a stable suspension with active compound content of 20% by weight.

2. Products to be Applied Undiluted

I Dusts 5 parts by weight of active compound (or composition) are ground finely and mixed intimately with 95 parts by weight of finely divided kaolin. This gives a dusting powder with an active compound content of 5% by weight.

J Granules (GR, FG, GG, MG)

0.5 parts by weight of active compound (or composition) are ground finely and associated with 99.5 parts by weight of carriers. Current methods here are extrusion, spray-drying or the fluidized bed. This gives granules to be applied undiluted with an active compound content of 0.5% by weight.

K ULV Solutions (UL)

10 parts by weight of active compound (or composition) are dissolved in 90 parts by weight of an organic solvent, for example xylene. This gives a product to be applied undiluted with an active compound content of 10% by weight.

Aqueous use forms can be prepared from emulsion concentrates, suspensions, pastes, wettable powders or water-dispersible granules by adding water.

It may furthermore be beneficial to apply the compositions of the invention alone or in combination with other herbicides, or else in the form of a mixture with other crop protection agents, for example together with agents for controlling pests or phytopathogenic fungi or bacteria. Also of interest is the miscibility with mineral salt solutions, which are employed for treating nutritional and trace element deficiencies. Other additives such as non-phytotoxic oils and oil concentrates may also be added.

USE EXAMPLES

The effect of the herbicidal compositions according to the invention of herbicides compound A and herbicide compound B and, if appropriate, herbicide compound C and/or safener on the growth of undesirable plants compared to the herbicidally active compounds alone was demonstrated by the following greenhouse experiments:

For the pre-emergence and post-emergence treatments, naptalam and the herbicide compounds B and optionally C and/or D, which had been suspended or emulsified in water, were applied by means of finely/evenly distributing spray nozzles. In all use examples, plants were grown in a greenhouse environment.

The herbicide compounds applied in the examples were used as commercially available formulations which have been diluted with tap water to a suitable concentration. Naptalam was used as a commercial SL formulation containing 240 g/l of naptalam (Alanap-L from Cheminova). Clopyralid was used as a commercial SL formulation containing 360 g/l of clopyralid (Stinger of Dow Agroscience). Picloram was used as a commercial SL formulation containing 240 g/l of picloram (Tordon 22K of Dow Agroscience). A mixture of 2,4-D+MCPP+Dicamba was used as a commercial SL formulation containing 283 g/l of 2,4-D, 63 g/l of MCPP and 25 g/l of Dicamba (Trimec Classic of PBI Gordon Corp.). Dicamba was used as a commercial SL formulation containing 480 g/l of Dicamba (Clarity BASF).

The evaluation for the plant damage or injury caused by the chemical compositions was carried out using a scale from 0 to 100%, when compared with the untreated control plants. Here, 0 means no damage and 100 means complete destruction of the plants. $I_{50}$ values were estimated from % injury data at different application rates by non-linear regression of log-logistic dose-response curves.

Colby's formula was applied to determine whether the composition showed synergistic action: S. R. Colby (1967) "Calculating synergistic and antagonistic responses of herbicide combinations", Weeds 15, p. 22 ff.

$$E = X + Y - (X \cdot Y/100)$$

where

X=effect in percent using herbicide A at an application rate a;

Y=effect in percent using herbicide B at an application rate b;

E=expected effect (in %) of A+B at application rates a+b.

The value E corresponds to the effect (plant damage or injury) which is to be expected if the activity of the individual compounds is just additive. If the observed effect is higher than the value E calculated according to Colby, a synergistic effect is present.

Example 1

Weed Control of Dicamba Plus Naptalam Mixtures

Seedlings of velvetleaf (*Abutilon theophrasti*; ABUTH), Palmer amaranth (*Amaranthus palmeri*; AMAPA), and common lambsquarters (*Chenopodium album*; CHEAL) were treated with postemergence applications of either dicamba at 140 or 280 g ae/ha, naptalam at 56 g ae/ha, or the combination of dicamba and naptalam at 140 and 56 g ae/ha, respectively, when they were 10-12 cm in height. All treatment mixtures contained 0.25% (v/v) non-ionic surfactant plus 1% (w/v) ammonium sulfate. Plants were placed in a completely randomized design with four replications per treatment. Percent injury data was collected 10 days after treatment (DAT). The results are summarized in table 1.

TABLE 1

Demonstration of dicamba potentiation through the addition of naptalam for the control of weeds.

| Treatment | Rate (g ae/ha) | Mean % Control[a] | | |
|---|---|---|---|---|
| | | ABUTH | AMAPA | CHEAL |
| Dicamba | 140 | 65.0 b | 80.0 b | 86.3 b |
| Naptalam | 56 | 0 c | 18.8 c | 0 c |
| Dicamba + Naptalam[b] | 140 + 56 | 95.8 a (65.0) | 100 a (83.7) | 97.8 a (86.3) |
| Dicamba | 280 | 91.3 a | 96.3 a | 98.5 a |

[a]Means followed by the same letter do not significantly differ (P = 0.05).
[b]The expected Colby equation weed control estimates for the combination of dicamba and naptalam are shown in parentheses following the observed responses.

As can be seen from the data in table 1, the combination of dicamba and naptalam provided significantly greater control of ABUTH, CHEAL, and AMAPA than each component individually. For each weed species, the observed control for the combination of dicamba and naptalam was greater than the estimates of expected control based on the Colby equation, thus demonstrating the potentiating effect of the herbicide mixture. Furthermore, the combination of dicamba and naptalam was similar to applications of dicamba at 280 g ae/ha, thus allowing a significant reduction of dicamba rates but still maintaining effective weed control.

Example 2

Rate Responses of Dicamba Plus Naptalam Combinations

Seedlings of ABUTH or CHEAL were treated with five different rates of dicamba between 0.14 and 140 g ae/ha when they were 10-12 cm in height. Naptalam was mixed with dicamba at rates of 0, 28, 35, 47, 70, or 140 g ae/ha to each dose-response series. All treatment mixtures included the addition of 0.25% (v/v) non-ionic surfactant and 1% (w/v) ammonium sulfate. Plants were placed in a completely randomized design with four replications per treatment. Percent injury data was collected 11 DAT and used to estimate the amount of dicamba necessary to obtain 50% injury ($I_{50}$). $I_{50}$ estimates for solo applications of dicamba ($I_{50}$ (—NPA)) were compared with $I_{50}$ estimates for the combined application of dicamba and naptalam ($I_{50}$ (+NPA)) to determine the relative increase of dicamba activity through the addition of naptalam. The results are summarized in table 2.

TABLE 2

Increased dicamba activity for the control of ABUTH or CHEAL through the addition of naptalam at different application rates.

| Naptalam | ABUTH | | CHEAL | |
|---|---|---|---|---|
| (g ae/ha) | $I_{50}$ (g ae/ha) | Fold-increase[a] | $I_{50}$ (g ae/ha) | Fold-increase[a] |
| 0 | 80.2 | 1.0 | 35.2 | 1.0 |
| 28 | 84.1 | 1.0 | 10.3 | 3.4 |
| 35 | 67.4 | 1.2 | 7.4 | 4.8 |
| 47 | 58.5 | 1.4 | 7.3 | 4.8 |
| 70 | 41.6 | 1.9 | 6.9 | 5.1 |
| 140 | 55.4 | 1.4 | 5.7 | 6.2 |

[a]Fold increase of dicamba activity = $I_{50}$(−NPA)/$I_{50}$(+NPA): lower $I_{50}$ estimates demonstrate increased dicamba activity.

As can be seen from the data in table 2, the results with ABUTH suggest approximately a 2-fold increase of dicamba activity when combined with naptalam. With CHEAL, up to a 6-fold increase of dicamba activity was obtained with the addition of naptalam.

Example 3

Preemergence Crop Selectivity of Dicamba Plus Naptalam

Winter wheat (*Triticum aestivum*, TRZAW) seeds were sown into soil, and the following day treated with five different rates of dicamba between 5.6 and 560 g ae/ha. Diflufenzopr (DFFP) or naptalam at rates of 224 g ae/ha was applied either alone or in combination with dicamba treatments. Following application, pots were placed in a completely randomized design with four replications per treatment. Percent injury data was collected 13 DAT. The results are summarized in table 3.

TABLE 3

Responses of TRZAW following preemergence applications of dicamba with or without the addition of DFFP or naptalam at 224 g ae/ha.

| | Mean % Injury* | | |
|---|---|---|---|
| Dicamba (g ae/ha) | Dicamba alone | +DFFP 224 g ae/ha | +Naptalam 224 g ae/ha |
| 0 | 0 f | 61.3 e | 0 f |
| 5.6 | 0 f | 67.5 de | 0 f |
| 17.7 | 0 f | 61.3 e | 0 f |
| 56.0 | 0 f | 68.8 cde | 0 f |
| 177.0 | 0 f | 83.8 ab | 0 f |
| 560.0 | 76.3 bcd | 93.8 a | 80.0 bc |

*Means followed by the same letter do not significantly differ (P = 0.05).

As can be seen from the data in table 3, responses of TRZAW to preemergence applications of dicamba were similar with or without the addition of naptalam at 224 g ae/ha. In contrast, the addition of DFFP at the same application rate as naptalam caused significant injury to TRZAW when applied preemergence.

Example 4

Postemergence Turf Selectivity of Dicamba Plus Naptalam

Seedlings of tall fescue (*Festuca arundinacea*, FESAR) or perennial ryegrass (*Lolium perenne*, LOLPE) were treated with five different rates of dicamba between 28 and 2800 g ae/ha when they were 10-14 cm in height. DFFP or naptalam at rates of 140 g ae/ha were applied either alone or in combination with dicamba treatments. All treatment mixtures contained 0.25% (v/v) non-ionic surfactant plus 1% (w/v) ammonium sulfate. Following treatment, plants were placed in a completely randomized design with four replications per treatment. Percent injury data was collected 13 DAT. The results are summarized in table 4.

TABLE 4

Responses of FESAR or LOLPE following postemergence applications of dicamba with or without the addition of DFFP or naptalam at 140 g ae/ha.

| | FESAR Mean % Injury[a] | | | LOLPE Mean % Injury[a] | | |
|---|---|---|---|---|---|---|
| Dicamba (g ae/ha) | Dicamba alone | +DFFP 140 g ae/ha | +Naptalam 140 g ae/ha | Dicamba alone | +DFFP 140 g ae/ha | +Naptalam 140 g ae/ha |
| 0 | 0 c | 38.8 b | 0 c | 0 e | 30.0 c | 0 e |
| 28.0 | 0 c | 43.8 b | 0 c | 0 e | 35.0 bc | 0 e |
| 88.5 | 2.5 c | 50.0 ab | 0 c | 0 e | 33.8 bc | 0 e |
| 280 | 5.0 c | 48.8 ab | 0 c | 0 e | 33.8 bc | 0 e |
| 885 | 7.5 c | 47.5 ab | 0 c | 0 e | 41.3 ab | 0 e |
| 2800 | 32.5 b | 63.8 a | 12.5 c | 7.5 de | 46.3 a | 12.5 d |

[a]Means within species followed by the same letter do not significantly differ (P = 0.05).

As can be seen from the data in table 4, responses of FESAR or LOLPE to postemergence applications of dicamba were similar with out without the addition of naptalam at 140 g ae/ha. In comparison to naptalam, the addition of DFFP caused significantly greater injury when applied either alone or when combined with dicamba.

Example 5

Postemergence Wheat Selectivity of Dicamba Plus Naptalam

Seedlings of TRZAW were treated with five different rates of dicamba between 14 and 1400 g ae/ha when they were 12-14 cm in height. In addition, DFFP or naptalam at 70 g ae/ha were applied either alone or in combination with dicamba treatments. All treatment mixtures contained 0.25% (v/v) non-ionic surfactant plus 1% (w/v) ammonium sulfate. Following treatment, plants were placed in a completely randomized design with four replications per treatment. Percent injury data was collected 8 DAT. The results are summarized in table 5.

TABLE 5

Responses of TRZAW following postemergence applications of dicamba with or without the addition of DFFP or naptalam at 70 g ae/ha.

| | TRZAW Mean % Injury* | | |
|---|---|---|---|
| Dicamba (g ae/ha) | Dicamba alone | +DFFP 70 g ae/ha | +Naptalam 70 g ae/ha |
| 0 | 0 g | 8.8 efg | 0 g |
| 14.0 | 0 g | 12.5 defg | 0 g |
| 44.0 | 2.5 fg | 15.0 cdef | 2.5 fg |
| 140 | 5.0 efg | 26.3 c | 3.8 efg |
| 440 | 25.0 cd | 45.0 b | 16.3 cde |
| 1400 | 50.0 ab | 61.3 a | 51.3 ab |

*Means followed by the same letter do not significantly differ (P = 0.05).

As can be seen from the data in table 5, responses of TRZAW to postemergence applications of dicamba were similar with out without the addition of naptalam at 70 g ae/ha. With rates of dicamba used in TRZAW productions situations, 140 g ae/ha, the addition of DFFP at 70 g ae/ha caused significantly greater injury when compared with adding naptalam at 70 g ae/ha or dicamba alone. These data demonstrate the crop safety of using dicamba plus naptalam combinations for postemergence weed control, which is not possible with combinations of dicamba and DFFP.

Example 6

Weed Control of Clopyralid or Picloram Plus Naptalam Mixtures

Seedlings of common amaranth (*Amaranthus retroflexus* AMARE) and common lambsquarters (*Chenopodium album*; CHEAL), each 8 to 10 cm in height, were treated with postemergence applications of either clopyralid at 53.5 g ae/ha, picloram at 5.6 g ae/ha or naptalam at 140 g ae/ha, or the combination of clopyralid and naptalam at 53.5 g ae/ha and 140 g ae/ha, or the combination of picloram and naptalam at 5.6 g ae/ha and 140 g ae/ha, respectively, when they were 8-10 cm in height. All treatment mixtures contained 0.25% (v/v) non-ionic surfactant. Plants were placed in a completely randomized design with four replications per treatment. Percent injury data was collected 10 days after treatment (DAT). The results are summarized in table 6.

TABLE 6

| | Rate | Mean % Control (10 DAT) | |
|---|---|---|---|
| Treatment | (g ae/ha) | AMARE | CHEAL |
| Control | 0 | 0 | 0 |
| Naptalam | 140 | 0 | 5 |
| Clopyralid | 53.5 | 23 | 25 |
| Naptalam + Clopyralid | 140 + 53.5 | 51 | 50 |
| Picloram | 5.6 | 43 | 43 |
| Naptalam + Picloram | 140 + 5.6 | 82 | 69 |

As can be seen from the data in table 6, the results with AMARE suggest approximately a 2-fold increase of clopyralid or picloram activity when combined with naptalam. With CHEAL, up to a 2-fold increase of clopyralid activity and a 1.6-fold increase of picloram activity was obtained with the addition of naptalam.

Example 7

Weed Control of 2,4-D+MCPP+Dicamba+Naptalam Mixtures

Seedlings of sunflower (*helianthus* sp. HELSS) were treated with postemergence applications of either a mixture of 2,4-D+MCPP+dicamba at 208+56+22 g ae/ha or at 83+22+9 g ae/ha, or naptalam at 56 g ae/ha, or the combination of 2,4-D+MCPP+dicamba and naptalam at 208+56+22+ 56 g ae/ha or at 83+22+9 g+56 g ae/ha, respectively, when they were 8-10 cm in height. All treatment mixtures contained 0.25% (v/v) non-ionic surfactant. Plants were placed in a completely randomized design with four replications per treatment. Percent injury data was collected 10 days after treatment (DAT). The results are summarized in table 7.

TABLE 7

| Treatment | Rate (g ae/ha) | Mean % Control (10 DAT) HELSS |
|---|---|---|
| Control | 0 | 0 |
| Naptalam | 56 | 12 |
| 2,4-D + MCPP + dicamba | 208 + 56 + 22 | 75 |
| Naptalam + 2,4-D + MCPP + dicamba | 56 + 208 + 56 + 22 | >95 |
| 2,4-D + MCPP + dicamba | 83 + 22 + 9 | 65 |
| Naptalam + 2,4-D + MCPP + dicamba | 56 + 83 + 22 + 9 | >95 |

Example 8

Weed Control of Clopyralid+Naptalam Mixtures

Seedlings of sunflower (*helianthus* sp. HELSS) were treated with postemergence applications of either clopyralid at 210 g ae/ha or at 105 g ae/ha, or naptalam at 56 g ae/ha, or the combination of clopyralid and naptalam at 210+56 g ae/ha or at 105+56 g ae/ha, respectively, when they were 8-10 cm in height. All treatment mixtures contained 0.25% (v/v) non-ionic surfactant. Plants were placed in a completely randomized design with four replications per treatment. Percent injury data was collected 10 days after treatment (DAT). The results are summarized in table 8.

TABLE 8

| Treatment | Rate (g ae/ha) | Mean % Control (10 DAT) HELSS |
|---|---|---|
| Control | 0 | 0 |
| Naptalam | 56 | 10 |
| Clopyralid | 210 | 83 |
| Naptalam + Clopyralid | 56 + 210 | 100 |
| Clopyralid | 105 | 28 |
| Naptalam + Clopyralid | 56 + 105 | 68 |

We claim:

1. A synergistic herbicidal composition comprising:
   a) a herbicide compound A which is selected from the group consisting of N-1-naphthylphthalamic acid (naptalam), the salts and esters thereof; and
   b) a herbicide compound B which is selected from the group consisting of
      b.1 quinolinecarboxylic acid herbicides;
      b.2 pyridinecarboxylic acid herbicides; and
      b.3 aminocyclopyrachlor, its salts and esters.

2. The composition of claim 1, wherein the weight ratio of the first herbicide compound A and the second herbicide compound B is from 50:1 to 1:50, and wherein each herbicide compound is calculated as the acid.

3. The composition of claim 1, wherein the herbicide compound B is selected from the group consisting of quinmerac, quinclorac, and the salts and esters thereof.

4. The composition of claim 1, wherein the herbicide compound B is selected from the group consisting of aminopyralid, clopyralid, picloram, triclopyr and fluoroxypyr, and the salts and esters thereof.

5. The composition of claim 1, wherein the herbicide compound B is selected from the group consisting of aminocyclopyrachlor and the salts and esters thereof.

6. The composition of claim 1, wherein the composition further comprises at least one herbicide compound C which is a synthetic auxin.

7. The composition as claimed in claim 6, wherein the at least one herbicide compound C is a synthetic auxin selected from the group consisting of
   c.1 benzoic acid herbicides;
   c.2 quinolinecarboxylic acid herbicides;
   c.3 pyridinecarboxylic acid herbicides;
   c.4 aminocyclopyrachlor, its salts and esters; and
   c.5 phenoxycarboxylic acid herbicides
   and mixtures thereof.

8. The composition of claim 1, wherein the composition further comprises a herbicide safener compound D.

9. The composition of claim 8, wherein the safener is selected from the group consisting of benoxacor, cyometrinil, cyprosulfamide, dichlormid, dicyclonon, dietholate, fenchlorazole, fenclorim, flurazole, fluxofenim, furilazole, mefenpyr, mephenate, naphthalic anhydride and oxabetrinil, and the salts and esters thereof.

10. A method for controlling undesirable vegetation, which comprises contacting a plant or its habitat with a composition of claim 1 to control the undersirable vegetation.

11. The method of claim 10, which comprises applying the composition before, during and/or after emergence of the plants, wherein the herbicide compounds A and B and optionally at least one herbicide compound C different from herbicide A and herbicide B and/or the compound D are applied simultaneously or in succession to control the undersirable vegetation.

12. An herbicide formulation comprising a composition of claim 1 and at least one solid or liquid carrier.

13. A synergistic method for controlling undesirable vegetation in plants, the method comprising applying a herbicidal composition comprising:
   a) a herbicide compound A which is selected from N-1-naphthylphthalamic acid (naptalam), and the salts and esters thereof; and
   b) a herbicide compound B which is selected from 3,6-dichloro-2-methoxybenzoic acid (dicamba), and the salts and esters thereof
   wherein composition is applied during and/or after the emergence of the plants and wherein the herbicide compounds A and B are applied simultaneously or in succession to control the undesirable vegetation.

14. The method of claim 13, wherein the weight ratio of the first herbicide compound A and the second herbicide compound B in the composition is from 50:1 to 1:50, and wherein each herbicide compound is calculated as the acid.

15. The method of claim 13, wherein the composition further comprises at least one herbicide compound C which is a synthetic auxin.

16. The method of claim 15, wherein the at least one herbicide compound C is a synthetic auxin selected from the group consisting of c.1 benzoic acid herbicides;
    c.2 quinolinecarboxylic acid herbicides;
    c.3 pyridinecarboxylic acid herbicides;
    c.4 aminocyclopyrachlor, its salts and esters; and
    c.5 phenoxycarboxylic acid herbicides and mixtures thereof.

17. The method of claim 15, wherein the composition further comprises a herbicide safener compound D.

18. The method of claim 17, wherein the safener is selected from the group consisting of benoxacor, cyometrinil, cyprosulfamide, dichlormid, dicyclonon, dietholate, fenchlorazole, fenclorim, flurazole, fluxofenim, furilazole, mefenpyr, mephenate, naphthalic anhydride and oxabetrinil, and the salts and esters thereof.

19. The method of claim 13, wherein the undesirable vegetation is in crop plants and in non-cropland areas, and wherein the non-cropland areas are selected from the group consisting of turf, pasture, fallow, rangeland, right-of-way areas, and forestry.

20. The method of claim 13 wherein the undesirable vegetation is in crop plants and in non-cropland areas, and wherein the crop plants are tolerant or resistant to the herbicide compound B and/or herbicide compound C different from herbicide A and herbicide B.

\* \* \* \* \*